United States Patent [19]
Zalewski et al.

[11] Patent Number: 6,133,242
[45] Date of Patent: Oct. 17, 2000

[54] INHIBITION OF EXTRACELLULAR MATRIX SYNTHESIS BY ANTISENSE COMPOUNDS DIRECTED TO NUCLEAR PROTO-ONCOGENES

[75] Inventors: Andrew Zalewski, Elkins Park; Yi Shi, Cheltenham, both of Pa.

[73] Assignee: Thomas Jefferson Univerisity, Philadelphia, Pa.

[21] Appl. No.: 08/461,366

[22] Filed: Jun. 5, 1995

Related U.S. Application Data

[63] Continuation-in-part of application No. PCT/US94/11853, Oct. 17, 1994, which is a continuation-in-part of application No. 08/138,637, Oct. 15, 1993, abandoned.

[51] Int. Cl.$^7$ .......................... A61K 48/00; C07H 21/04; C07H 21/02; C12Q 1/68
[52] U.S. Cl. .................. 514/44; 435/6; 435/91.1; 435/240.2; 435/325; 435/455; 435/375; 536/23.1; 536/24.1; 536/24.5
[58] Field of Search .......................... 435/6, 91.1, 172.1, 435/240.2, 455, 375, 325; 514/44; 536/23.1, 24.5, 24.1

[56] References Cited

U.S. PATENT DOCUMENTS

| | | | |
|---|---|---|---|
| 5,245,022 | 9/1993 | Weis et al. | 536/24.5 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |
| 5,593,974 | 1/1997 | Rosenberg et al. | 514/44 |
| 5,756,476 | 5/1998 | Epstein et al. | 514/44 |

FOREIGN PATENT DOCUMENTS

| | | |
|---|---|---|
| WO 90/03189 | 4/1990 | WIPO . |
| WO 92/05305 | 1/1993 | WIPO . |
| WO 93/08845 | 5/1993 | WIPO . |
| WO 94/15645 | 7/1994 | WIPO . |
| WO 94/15646 A1 | 7/1994 | WIPO . |
| WO 94/15943 | 7/1994 | WIPO . |
| WO 94/26888 | 11/1994 | WIPO . |
| WO 94/28721 | 12/1994 | WIPO . |
| WO 95/10305 A1 | 4/1995 | WIPO . |

OTHER PUBLICATIONS

Gura, T. "Antisense Has Growing Pains", Science vol. 270: 575–577, Oct. 27, 1995.
Wu Pong, S. "Oligonucleotides: Opportunities for Drug Therapy Research", Pharmaceutical Technology. vol. 18: 102–114, Oct. 1994.
Stull, R. et al "Antigene, Ribozyme and Aptamer Nucleic Acid Drugs: Progress and Prospects", Pharmaceutical Research. vol. 12(4): 465–483, 1995.
Bennet, F. "Antisense Research", Science vol. 271:434, Jan. 26, 1996.
Westermann, B. et al "Inhibition of Expression of SV40 virus large T–antigen byAntisense Oligonucleotides", Biomed. Biochim. Acta. vol. 48: 85–93, 1989.
Milligan, J. "Current Concepts in Antisense Drug Design", J. Medicinal Chemistry. vol. 36(14): 1923–1937, Jul. 9, 1993.
Miller, N. et al "Gene Transfer and Antisense Nucleic Acid Techniques", Parisitology Today. vol. 10(3): 92–97, 1994.
Rojanasakul, Y. "Antisense Oligonucleotide Therapeutics: Drug Delivery and Targeting", Advanced Drug Delivery Reviews. vol. 18: 115–131, 1996.
Burgess, T. et al "The Antiproliferative Activity of c–myb and c–myc Antisense Oligonucleotides in Smooth Muscle Cells is Caused by a Nonantisense Mechanism", PNAS vol. 92: 4051–4055, Apr. 1995.
Kulka, M. et al Site Specificity of the Inhibitory Effects of Oligonucleotides Complimentary to the Acceptor Splice Junction of Herpes Simplex Virus Type 1 Immediate Early mRNA 4. PNAS vol. 86: 6868–6872, Sep. 1989.
Wagner, R. "Gene Inhibition Using Antisense Oligonucleotides", Nature vol. 372: 333–335, Nov. 24, 1994.
Watson et al., "Inhibition of cell adhesion to plastic substratum by phosphorothioate oligonucleotide", Experimental Cell Research, 202(2) 391–7 XP000644735 (Oct. 1992).
Wilensky et al., "Methods and devices for local drug delivery in coronary and peripheral arteries", Trends in Cardiovascular Medicine, vol. 3, 163–70, XP000644584 (Sep.–Oct. 1993).
Shi et al., "Regulation of extracellular matrix synthesis by antisense oligomers targeting the c–myc", Circulation 90(4) (Part 2) Abstract 2767, XP000644592 (Oct. 1994).
Shi et al., "C–myc antisense oligomers reduce neointima formation in porcine coronary arteries", Journal of the American College of Cardiology 0 (Spec. Issue), 395A, Abstract 798–5 XP000644587 (Feb. 1994).
Abe et al. "Biochem and Biophysical Research Communications", 198:1:16–24, Jan. 14, 1994.
Agrawal, "Pharmacokinetics, biodistribution, and stability of ligodeoxynucleotide phosphorothioates in mice", Proc. Natl. Acad. Sci. USA vol. 88, pp. 7585–7599, Sep. 1991.
Agrawal, et al., "Antisense Oligonucleotide Based Therapeutic Approach: From Laboratory to Clinical Trials", Antisense Therapy: Efficacy and Delivery of Antisense & Ribozine Oligonucleotide (Feb. 23–25, 1995 London).
Ang et al., "Collagen synthesis by cultured rabbit aortic smooth–muscle cells", Biochem 265:461–469 (1990).

(List continued on next page.)

Primary Examiner—John S. Brusca
Assistant Examiner—Sean McGarry
Attorney, Agent, or Firm—Seidal, Gonda, Lavorgna & Monaco, PC

[57] ABSTRACT

A method and compounds are provided for inhibiting the synthesis of extracellular matrix proteins. Compounds of the invention comprise antisense oligonucleotides specific for nuclear proto-oncogenes. Preferably, antisense compounds of the invention are selected from the group consisting of c-myc and c-myb and are locally administered. The invention finds use in the treatment of a variety of disorders, including sclerotic disorders and restenosis, associated with the inappropriate synthesis of extracellular matrix proteins, particularly collagen.

25 Claims, 23 Drawing Sheets

OTHER PUBLICATIONS

Baringa M., "Gene Therapy for Clogged Arteries Passes Test in Pigs" *Science* 265:738, Aug. 5, 1994.

Bauters et al., "Proto–oncogene expression in rabbit aorta after wall injury First marker of the cellular process leading to restenosis after angioplasty" *European Heart Journal*, 13:556–559 (1992).

Bayever, et al., "Oligonucleotides In The Treatment of Leukemia" *Hematological Oncology*, vol. 12:9–14, (1994).

Beldekas et al., "Cell Density and Estradiol Modulation of Procollagen Type III in Cultured Calf Smooth Muscle Cells*" *The Journal of Biological Chemistry*, 257:20:12252–12256, Oct. 25, 1982.

Biro et al., "Inhibitory Effects of Antisense Oligonucleotides targeting c–myc mRNA on Smooth Muscle Cell Proliferation and Migration", *Proc. Natl. Acad. Sci.* 90:654–658 (1993).

Brown et al., "Expression of the c–myb Proto–oncogene in Bovine Vascular Smooth Muscle Cells*" *The Journal of Biological Chemistry*, 267:7:4625–4630, Mar. 5, 1992.

Castellot, "Effect of Heparin on Vascular Smooth Muscle Cells . . . ", *Journal of Cellular Physiology*, 124:21–28 (1985).

Chang and Sonenshein, "Increased Collagen Gene Expression in Vascular Smooth Muscle Cells Cultured in Serum or Isoleucine Deprived Medium", *Matrix*, vol. 11:242–251 (1991).

Collins et al., "c–myc Antisense Oligonucleotides Inhibit the Colony–Forming Capacity of Colo 320 Colonic Carcinoma Cells", *Journal of Clinical Investigation*, vol. 89:1523–1527, (1992).

Crooke, "Therapeutic Applications of Oligonucleotides", *Annu. Rev. Pharmacol. Toxicol*, 32:329–376, (1992).

de Fabritiis, et al., In vitro Purging with BCR–BRL Antisense Oligonucleotide does not Prevent Haematologic Resonstitution After Autologous Bone Marrow Transplantation, *Leukemia*, 9(4):662–664, (1995).

Dreher et al., "Expression of antisense transcripts encoding an extracellular matrix protein by stably transfected vascular smooth muscle cells" *Eur. J. Cell Biol.* 54 (1991) pp. 1–9.

Ebbecke et al., "Antiproliferative effects of a c–myc antisense oligonucleotide on human arterial smooth muscle cells" *Basic Res Cardiol*, 87:585–591 (1992).

Ebbecke et al., "Inhibition of Human Arterial Smooth Muscle Cell Proliferation by a c–myc Antisense Oligonucleotide", *Abstract, XIIIth Congress of the European Society of Cardiology* Aug. 18–22, 1991, Amsterdam, The Netherlands (No. 677).

Ebecke et al., "In vitro Assessment of Polyactides as Slow Release Drug Carriers", *Supplement to Circulation*, vol. 84(4), Abstract No. 0285, (1991).

Edelman et al., "Perivascular and Intravenous Administration of Basic Fibroblast Growth Factor: Vascular and Solid Organ Deposition", *Proc. Natl. Acad. Sci.*, vol. 90:1513–1517, (1993).

Edelman et al., "Effect of Controlled Adventitial Heparin Delivery on Smooth Muscle Cell Proliferation Following Endothelial Injury", *Proc. Natl. Acad. Sci.*, vol. 87:3773–3777, (1990).

Edelman et al., "c–myc in Vasculoproliferative Disease", *Circulation Research*, vol. 76(2): 176–182, (1995).

Epstein et al., "Inhibition of Cell Proliferation using Antisense Oligonucleotides. (Use of c–myc Antisense to Inhibit Cell Proliferation Associated with Restenosis)" *NTIS Publication* PB93–100576 (Jan. 1, 1993), pp. 1–38.

Fard et al., "Mechanisms of Neointimal Reduction after Transcatheter Delivery of c–myc Antisense Oligomers" *Circulation*, 90:I–191, abstract No. 1022, Nov. 1994.

Farquharson et al., "Immunolocalization of Collagen Types I and III in the Arterial Wall of the Rat", *Histochemical Journal*, 21(3):172–178 (1989).

Fernandez–Ortiz et al., "A New Approach for Local Intravascular Drug Delivery", *Circulation*, vol. 89(4):1518–1522, (1994).

Fox et al., "Fish Oils Inhibit Endothelial Cell Production of Platelet–Derived Growth Factor–Like Protein" *Science*, 241:453–456 (1988).

Gabbiani et al., "Actin Expression in Smooth Muscle Cells of Rat Aortic Intimal Thickening, Human Atheromatous Plaque, and Cultured Rat Aortic Media" *J. Clin Invest.*, 73:148–152, Jan. 1984.

Gazin et al., "Nucleotide sequence of the human c–myc locus: provocative open reading frame within the first exon" *The EMBO Journal*, 3:2:383–387, 1984.

Hanke et al., "Prolonged Proliferative Response of Smooth Muscle Cells after Experimental Intravascular Stenting: A Stent Wire Related Phenomenon" *Abstract, Supplement to Circulation*, 86:4:I–186, Oct. 1992 (0742).

Hiija, et al., Biologic and Therapeutic Significance of MYB Expression in Human Melanona, *Proc. Natl. Acad. Sci.*, vol. 91:4499–4503, (1994).

Holmes et al., "restenosis," from PTCA (Percutaneous Transluminal Coronary Angioplasty), Chapter 12:161–175, (Viliestra & Holmes) (1990).

Holt et al. An Oligomer Complementary to c–myc mRNA Inhibits Proliferation of HL–60 Promyelocytic Cells and Induces Differentiation. *Molecular and Cellular Biology* 8:963–973 (1988).

Hutchinson et al., "Inhibition of Human Vascular Smooth Muscle Cell Proliferation Using c–myc Antisense Oligonucleotides" *Abstract, Supplement to Circulation*, 86:4:I–226, Oct. 1992 (0898).

Hutchinson et al., "Inhibition of Porcine Vascular Smooth Muscle Cell Proliferation Using c–myc Antisense Oligonucleotides" *Abstract, JACC*, 21:2:327A Feb. 1993 (786–5).

Iversen, "In vivo Studies with Phosphorothioate Oligonucleotides: Pharmacokinetics Prologue", *Anti–Cancer Drug Design*, 6:531–538, (1991).

Karas et al. "Coronary Intimal Proliferation After Balloon Injury and Stenting in Swine: An Animal Model of Restenosis" *JACC*, 20:2:467–74, Aug. 1992.

Kindy et al., "Regulation of Oncogene Expression in Cultured Aortic Smooth Muscle Cells." *J. Biol. Chem.* 261:12865–12868 (1986).

Kovalik et al., "Correction of Central Venous Stenoses: Use of Angioplasty and Vascular Wallstents", *Kidney International*, 45:1177–1181, (1994).

Langer et al., "Controlled Release and Magnetically Modulated Release Systems for Macromolecules", *Methods in Enzymology*, 112:399–422 (1985).

Libby et al., "A Cascade Model for Restenosis", Supplemental III Circulation, 86(6):III47–III52, (1992).

Majesky et al., "Production of Transforming Growth Factor $\beta_1$ during Repair of Arterial Injury" *J. Clin Invest.*, 88:904–910, Sep. 1991.

Majesky et al., "Rat Carotid Neointimal Smooth Muscle Cells Reexpress a Developmentally Regulated mRNA Phenotype During Repair of Arterial Injury" *Circulation Research*, 71:4:759–768, Oct. 1992.

Marcu et al., "myc Function and Regulation", *Ann. Rev. Biochem*, 61:809–860 (1992).

McCullagh et al., "Collagen Characterisation and Cell Transformation in Human Atherosclerosis", *Nature*, 258:73–75 (1975).

McGraw et al., "Sequence–Dependent Oligonucleotide–Target Duplex Stabilities: Rules from Empirical Studies with a Set of Twenty–Mers" *BioTechniques*, 8:6:674–678 (1990).

Miano et al. "Early Proto–Oncogene Expression in Rat Aortic Smooth Muscle Cells Following Enothelial Removal", *Am. J. Pathology*, 137:4:61–765 (1990).

Mirabelli et al., "In vitro and in vivo pharmacologic activities of antisense oligonucleotides" *Anti–Cancer Drug Design* 6:647–661, Dec. 1991.

Miyashi et al., "Distribution of the Collagen Binding Heat–hock Protein in Chicken Tissues" *The Journal of Histochemistry and Cytochemistry*, 40:7:1021–1029, 1992.

Morishita et al., "Single intraluminal delivery of antisense cdc2 kinase and proliferating–cell nuclear antigen oligonucleotides results in chronic inhibition of neointimal hyperplasia" *Proc. Natl. Acad. Sci.*, 90:8474–8478 (1993).

Muller et al., "Experimental Models of Coronary Artery Restenosis" *JACC*, 19:2:418–32, Feb. 1992.

Nabel et al., "Direct Gene Transfer with DNA–Liposome Complexes in Melanona: Expression, Biologic Activity, and Lack of Toxicity in Humans", *Proc. Natl. Acad. Sci.*, vol. 90:11307–11311, (1993).

O'Brien et al., "Proliferation in Primary and Restenotic Coronary Atherectomy Tissue" *Circulation Research*, 73:2:223–231, Aug. 1993.

O'Brien et al., "Inhibition of Cell Proliferation by C–myc Antisense Oligomers Following Surgical Revascularization" *Circulation* 92:8:1297, abstract No. 1414 (Nov. 1995).

Offensperger et al., "In vivo Inhibition of Duck Hepatitis B Virus Replication and Gene Expression by Phosphorothioate Modified Antisense Oligodeoxynucleotides", *The EMBO Journal*, 12(3) 1257–1262, (1993).

Ohno et al., "Gene Therapy for Vascular Smooth Muscle Cell Proliferation After Artierial Injury" *Science*, 265:781–784, Aug. 5, 1994.

Pickering et al., "Proliferative Activity in Peripheral and Coronary Atherosclerotic Plaque among Patients Undergoing Percutaneous Revascularization" *J. Clin. Invest.* 91:1469–1480, Apr. 1993.

Pickering et al., "Collagen Elaboration Following Balloon Angioplasty—Evidence for Rapid Expression and Deposition" *Abstract, JACC*, Feb. 1994:1A–484A, p. 235A (No. 906–37).

Plante et al., "Porous Balloon Catheters for Local Delivery: Assessment of Vascular Damage in a Rabbit Iliac Angioplasty Model" *JACC*, 24:3:820–824, Sep. 1994.

Powell et al., "Inhibitors of Angiotensin–Converting Enzyme Prevent Myointimal Proliferation After Vascular Injury", *Science*, 245:186–188, (1989).

Ratajczak et al., "In vivo treatment of heman leukemia in a scid mouse model with c–myb antisense oligodeoxynucleotides", *Proc. Natl. Acad. Sci.*, 89:11823–11827 (1992).

Ratajczak et al., "Oligonucleotide Therapeutics for Human Leukemia, Antisense Therapy", *Efficacy and Delivery of Antisense & Ribozyme Oligonucleotides*, (Presented Feb. 23–24, 1995, London).

Rhine et al., "Polymers for Sustained Macromolecule Release: Procedures to Fabricate Reproducible Delivery Systems and Control Release Kinetics", *Journal of Pharmaceutical Sciences*, 69(3):265–270, (1980).

Rhodes, "The Blood Vessell", *Chapter 20 in Weiss et al. Editors, Collagen in Health and Disease*, (Churchill Livingstone, Edinburgh, 1981).

Riessen et al., "Prospects for Site–Specific Delivery of Pharmacologic and Molecular Therapies" *JACC*, 23:5:1234–1244, Apr. 1994.

Ross et al., "I. Cell Constitution and Characteristics of Advanced Lesions of the Superficial Femoral Artery" *Human Atherosclerosis*, 114:1:79–93.

Ross, "The Pathogenesis of Atherosclerosis: a Prespective for the 1990s", *Nature*, 362:801–809 (1993).

Rothenberg et al., "Oligodeoxynucleotides as Anti–Sense Inhibitors of Gene Expression: Therapeutic Implications", *Commentary*, 81(20):1539–1544, (1989).

Schwartz et al., "Restenosis After Balloon Angioplasty" *Circulation*, 82:6:2190–2200, Dec. 1990.

Shi et al., "Gene Transfer Into Coronary Vasculature Using Transcatheter Delivery" *Abstract, The Faseb Journal*, 7:4:A562, Feb. 23, 1993 (3261).

Shi et al., "Maximizing Gene Transfer Into Vascular Smooth Muscle Cells" *Abstract, JACC*, 21:2:209A, Feb. 1993 (900–37).

Shi et al., "Transcatheter Delivery of c–myc Antisense Oligomers Reduces Neointimal Formation in a Porcine Model of Coronary Artery Balloon Injury" *Circulation*, 90:2:944–950, Aug. 1994.

Shi et al., "Downregulation of c–myc Expression by Antisense Oligonucleotides Inhibits Proliferation of Human Smooth Muscle Cells" *Circulation*, 88:3:1190–1195, Sep. 1993.

Shi et al., "Inhibition of Type I Collagen Synthesis in Vascular Smooth Muscle Cells by c–myc Antisense Oligomers", *Circulation*, 90(4) (Part 2): Nos. 0787 & 2767, (1994).

Shi et al., "Safety and Efficacy of Transcatheter Delivery of C–myc Antisense Oligomers in the Coronary Vasculature" *Circulation* 90:I–393, abstract No. 2110 (Nov. 1994).

Shi et al., "C–myc Antisense Oligomers Reduce Neointima Formation in Porcine Coronary Arteries" *Journal of the American College of Cardiology* Special issue, p. 395A, abstract No. 798–5 (Mar. 1994).

Simons et al., "Antisense Nonmuscle Myosin Heavy Chain and c–myb Oligonucleotides Suppress Smooth Muscle Cell Proliferation in Vitro", *Circulation Research*, 70(4):835–843, (1992).

Simons et al., "Antisense c–myb Oligonucleotides Inhibit Intimal Arterial Smooth Muscle Cell Accumulation In Vivo", *Nature*, 359:67–70 (1992).

Simons et al., "Antisense Proliferating Cell Nuclear Antigen Oligonucleotides Inhibit Intimal Hyperplasia in a Rat Carotid Artery Injury Model" *J. Clin. Invest.* 93:2351–2356, Jun. 1994.

Skorski, et al., "Suppression of Philadelphia Leukemia Cell Growth in Mice by BCR–ABL Antisense Oligodeoxynucleotide", *Proc. Natl. Acad. Sci.*, vol. 91:4504–4508 (Sep. 1994).

Snoeckx et al., "Expression and cellular distribution of heat–shock and nuclear oncogene proteins in rat hearts" *The American Physiologcal Society*, H1443–H1451, 1991.

Speir et al., "A Strategy for Employing Antisense Oligonucleotides in Inhibit Smooth Muscle Cell Proliferation; Cloning and Sequencing Some Relevant Genes and Preliminary Results of Antisense ODNs Targeted to c–myc and PCNA" *NIH Research Festival Poster*, Sep. 23–24, 1991.

Speir et al., "Inhibition of Smooth Muscle Cell Prolifereation by an Antisense Oligodeoxynucleotide Targeting the Messenger RNA Encoding Proliferating Cell Nuclear Antigen", *Circulation*, 86(2):538–547, (1992).

Stein et al., "Antisense Oligonucleotides as Therapeutic Agents–Is the Bullet Really Magical?", *Science*, 261:1004–1012, (1993).

Stepp et al., "Complex Regulation of Collagen Gene Expression in Cultured Bovine Aortic Smooth Muscle Cells" *The Journal of Biological Chemistry*, 261:14:6542–6547, May 15, 1986.

Thompson et al., "Levels of c–myc oncogene mRNA are invariant throughout the cell cycle" *Nature*, 314:363–366, Mar. 28, 1985.

Uhlman and Peyman, "Antisense Oligonucleotides: a New Therapeutic Principle", *Chemical Reviews* 90:543–584 (1990).

Van der Rest et al., "Collagen Family of Proteins", *FASEB J.* 5:2814–2823 (1991).

Villa et al., "Effects of Antisense c–myb Oligonucleotides on Vascular Smooth Muscle Cell Proliferation and Response to Vessel Wall Injury", *Circularation Research*, 76(4):505–513, (1995).

Vliestra et al., Chapter 9 "Objective Assessment of Results, Chapter 12 Restenosis", *PTCA (Percutaneous Transluminal Coronary Angioplasty)*, (Davis Company, Philadelphia, 1987), pp. 105–126.

Walker et al., "Producation of Platelet–Derived Growth Factor–Like Molecules by Cultured Arterial Smooth Muscle Cells Accompanies Proliferation After Arterial Injury", *Proc. Natl. Acad. Sci.*, 83:7311–7315, (1986).

Weiss, "Upping the Antisense Ante", *Science News*, pp. 108–109 (Feb. 16, 1991).

Wetmur, "DNA probes: Applications of the principles of nucleic acid hybridization", *Critical Reviews in Biochemistry and Molecular Biology*, 26:227–259 (1991).

Whitesell et al., "Stability, Clearance, and Disposition of Intraventricularly Administered Oligodeoxynucleotides: Implications for Therapeutic Application Within the Central Nervous System", *Proc. Natl. Acad. Sci.*, 90:4665–4669, (1993).

Wickstrom et al., "Human Promyelocytic Leukemia HL–60 Cell Proliferation and c–myc Protein Expression are Inhibited by an Antisense", *Proc. Natl. Acad. Sci.*, 85:1028–1032 (1988).

Wickstrom et al., "Antisense DNA Methylphosphonate Inhibition of c–myc Gene Expression in Trangenic Mice" *Abstract, The Faseb Journal*, 5:5:A1433, Mar. 15, 1991 (No. 6218).

Windsor et al., "Smooth Muscle Proliferation During Neointimal Development After PTCA in Swine: Identification of Site and Sequence Using Proliferating Cell Nuclear Antigen Staining" *Abstract, JACC*, Feb. 1994:1A–484A, p. 235A.

Wolinsky et al., "Use of a Perforated Balloon Catheter to Deliver Concentrated Heparin Into the Wall of the Normal Canine Artery" *JACC*, 15:5:475–81, Feb. 1990 (No. 900–35).

Woolf et al., "Specificity of Antisense Oligonucleotides in vivo", *Proc. Natl. Acad. Sci.*, 89:7305–7309, (1992).

Vu and Hirschbein, "Internucleotide Phosphite Sulfurization With Tetraethylthiuram Disulfide. Phosphorothioate Oligonucleotide Synthesis Via Phosphoramidite Chemistry" *Tetrahedron Lett.*, 32:3005–3008 (1991).

Zamecnik et al., "Inhibition of Rous Sarcoma Virus Replicationa nd Cell Transformation by a Specific Oligodeoxynucleotide", *Proc. Natl. Acad. Sci.*, 75(1):280–284, (1978).

Zeymer et al., "Proliferating Cell Nuclear Antigen Immunohistochemistry in Rat Aorta After Balloon Denudation" *PCNA Immunohistochemistry in Rat Aorta, AIP*, Sep. 1992, 141:3:685–690.

Zon, "Oligonucleotide Analogues as Potential Chemotherapeutic Agents", *Pharmaceutical Research*, 5(9):539–549, (1988).

INHIBITION OF EXTRACELLULAR MATRIX SYNTHESIS BY ANTISENSE COMPOUNDS DIRECTED TO NUCLEAR PROTO-ONCOGENES

CROSS REFERENCE TO RELATED APPLICATIONS

This application is a continuation in part of PCT Application PCT/US94/11853, filed Oct. 17, 1994, which is a Continuation In Part of U.S. application Ser. No. 08/138,637, filed Oct. 15, 1993 now abandoned.

The invention relates generally to oligonucleotides and their use as therapeutic agents, and more particularly to the use oligonucleotide antisense and anti-gene compounds to inhibit the synthesis of extracellular matrix proteins, particularly in fibroblasts and smooth muscle cells.

BACKGROUND

Extracellular matrix consists primarily of collagens, proteoglycans, elastin, and fibronectin. The inappropriate synthesis of extracellular matrix proteins and/or the synthesis of aberrant forms of such proteins is associated with wide range of deleterious conditions, including many rare heritable diseases as well as more commonly acquired disorders, such as fibrotic skin disease, pulmonary fibrosis, osteoarthritis, vascular restenosis, and the like, e.g., Weiss and Jayson, Editors, Collagen in Health and Disease (Churchill Livingstone, Edinburgh, 1982); Gardner, Editor, Pathological Basis of the Connective Tissue Diseases (Lea & Febiger, Philadelphia, 1992).

Many of these conditions are associated with very complex biological responses to physical, chemical, and/or biological insults. Such responses include the proliferation and migration of a variety of cell types and the synthesis of a growth factors that contribute to or modify the response. For example, vascular disorders, such as atherosclerosis and vascular restenosis, are associated with local cell proliferation and migration, as well as the production of several classes of structural proteins and many growth factors, including platelet-derived growth factor, basis fibroblastic growth factor, tumor necrosis factor $\alpha$, interleukin-1, prostaglandins, and a variety of proto-oncogenes, e.g., Ross, Nature, 362: 801–809 (1993); and Morishita et al, Proc. Natl. Acad. Sci., 90:8474–8478 (1993). Unfortunately, the precise role of these factors in the various disease processes is not well understood.

The tremendous economic impact of disorders associated with inappropriate production of extracellular matrix proteins, especially vascular disorders, has served as a strong impetus to develop drugs or other methods of treatment to cure or ameliorate their debilitating effects. In this class of disease, as well as others, where a disease condition is associated with the apparent aberrant expression of a endogenous gene, the use of so called antisense compounds provides many advantages, e.g. Milligan et al, J. Med. Chem., 36:1923–1937 (1993); Uhlmann and Peyman, Chemical Reviews, 90:543–584 (1990); Goodchild, Bioconjugate Chemistry, 1:165–187 (1990); Crooke, Ann. Rev. Pharmacol. Toxicol., 32:329–376 (1992); Stein et al, Science, 261:1004–1012 (1993); and the like.

A particularly compelling advantage of the antisense approach is that one need not carry out one or more initial screening steps to identify candidate compounds capable of binding to a therapeutic target. If the aberrant expression of a gene is known to cause a disease for which a drug is sought, then the structures of candidate antisense drugs are determined automatically from the nucleotide sequence of the aberrantly expressed gene. One need only provide an oligonucleotide or an analog thereof capable of forming a stable duplex or triplex with such a gene, or associated target polynucleotide, based on Watson Crick or Hoogsteen binding, respectively. The specifically bound antisense compound then either renders the respective targets more susceptible to enzymatic degradation, blocks translation or processing, or otherwise blocks or inhibits the function of a target polynucleotide.

It would be highly advantageous if particular genes were identified whose expression were causally related to the synthesis of structural proteins, such as collagen, that contribute to disease conditions. Such identification would immediately lead to the prospect of treatments for a number of disorders associated with the excess synthesis of such proteins by the antisense approach.

SUMMARY OF THE INVENTION

The invention provides a method of treating disorders associated with the inappropriate synthesis of extracellular matrix proteins, particularly collagen. The method comprises the step of administering to an individual in need of such treatment an effective amount of one or more antisense oligonucleotides specific for nuclear proto-oncogenes. As defined more fully below, an "antisense oligonucleotide specific for 30 a nuclear proto-oncogene" is an oligonucleotide having a sequence (i) capable of forming a stable duplex with a portion of an mRNA transcript of a nuclear proto-oncogene, or (ii) capable of forming a stable triplex with a portion of a nuclear proto-oncogene. Preferably, the antisense oligonucleotides of the invention form stable duplexes with portions of an mRNA transcript of a nuclear proto-oncogene. More preferably, antisense oligonucleotides of the invention are specific for mRNA transcripts of c-myc or c-myb proto-oncogenes. Most preferably, antisense oligonucleotides of the invention are specific for mRNA transcripts of the c-myc proto-oncogene.

Preferably, c-myc antisense oligonucleotides are administered locally to the site at which the inappropriate synthesis of extracellular matrix proteins takes place.

Blots demonstrate collagen a chains. Lane 1:no oligonucleotides; Lane 2: sense oligonucleotides; Lane 3: 4 bp mismatched ODN; Lane 4: scrambled oligonucleotides; Lane 5: antisense targeting the translation initiation regions of c-myc mRNA (position 559–573, AS1); Lane 6: antisense targeting exon 1 (position 400–419, AS2) and Lane 7: antisense targeting translated region in exon 3 (position 1264–1283, AS3). Lower panel: Histograms depicting percent change of control values (no oligonucleotides) obtained from densitometric measurements of 3 separate experiments (mean±SEM). Mis: 4 bp mismatched oligonucleotides; Scr: scrambled oligonucleotides.

Figure 6:
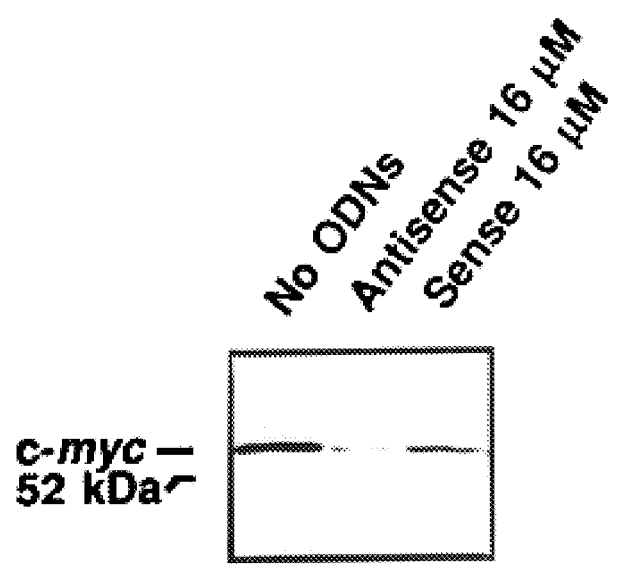

FIG. 6 describes the inhibition of c-myc protein by antisense oligonucleotides (AS1). Post-confluent smooth muscle cells were incubated with or without antisense oligonucleotides for 24 hours. The p62c-myc was determined by immunoprecipitation of [$^{35}$S]methionine-labeled nuclear extracts and it is shown on autoradiogram of SDS-polacrylamide gel.

Figure 7:
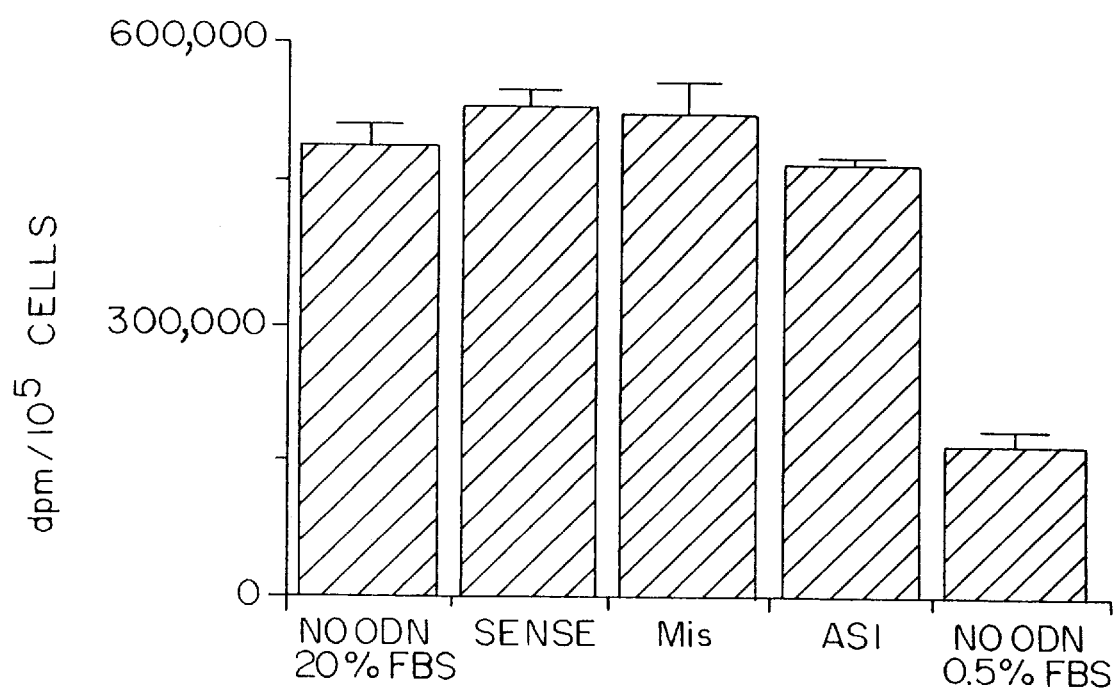

FIG. 7 describes metabolic state of smooth muscle cells following oligonucleotides. Cells were preincubated with or without oligonucleotides (16 $\mu$M) for 4 hours and labeled with [35$_S$]methionine for 16 hours. The radiolabeled proteins were measured after TCA precipitation. Antisense oligonucleotides showed no effect on methionine incorporation into proteins demonstrating normal metabolic activity of smooth muscle cells. Data represent dpm/105 cells (mean±SEM of 2 separate experiments), S: sense; MIS: mismatched; SCR: scrambled; ASI: antisense oligonucleotides targeting translation initiation region of c-myc mRNA.

Figure 8:
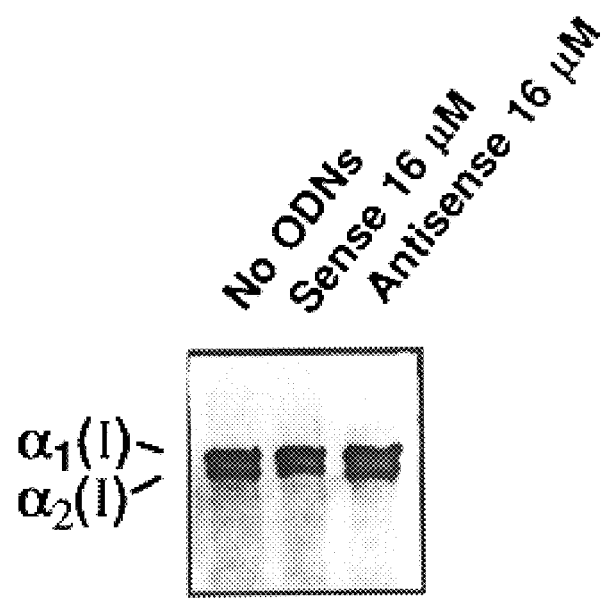

FIG. 8 describes the recovery of type I collagen after the removal of c-myc antisense oligonucleotides (AS1). smooth muscle cells were incubated with or without oligonucleotides (16 $\mu$M) for 24 hours. After 3 washes, medium without oligonucleotides was added and collected 24 hours thereafter. Type I collagen was determined by Western blot after pepsin digestion. A complete recovery of type 1 collagen is seen after the removal of c-myc antisense oligonucleotides.

Figure 9:
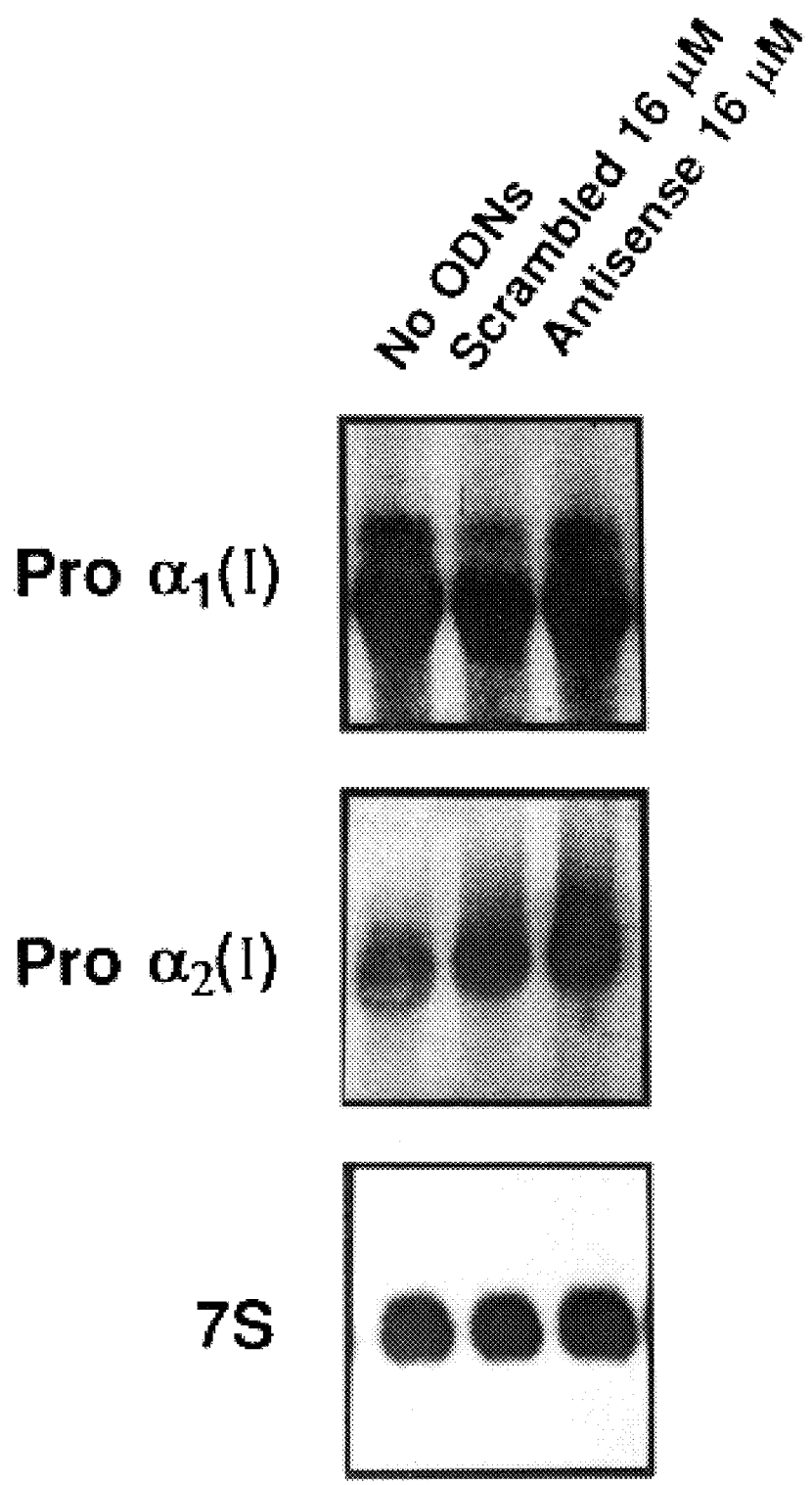

FIG. 9 describes the effect of c-myc antisense oligonucleotides on pro $\alpha_1$(I) and pro $\alpha_2$(I) mRNA levels. Total RNA was isolated from smooth muscle cells incubated with or without oligonucleotides (16 $\mu$M) for 24 hours and analyzed by Northern blot (10 $\mu$g/lane). Antisense oligonucleotides (AS1) had no effect on procollagen $\alpha_1$(I) and procollagen $\alpha_2$(I) mRNA levels. Experiments carried out at 6 hours after antisense treatment yielded similar results. 7S RNA showed no change.

Figure 10:
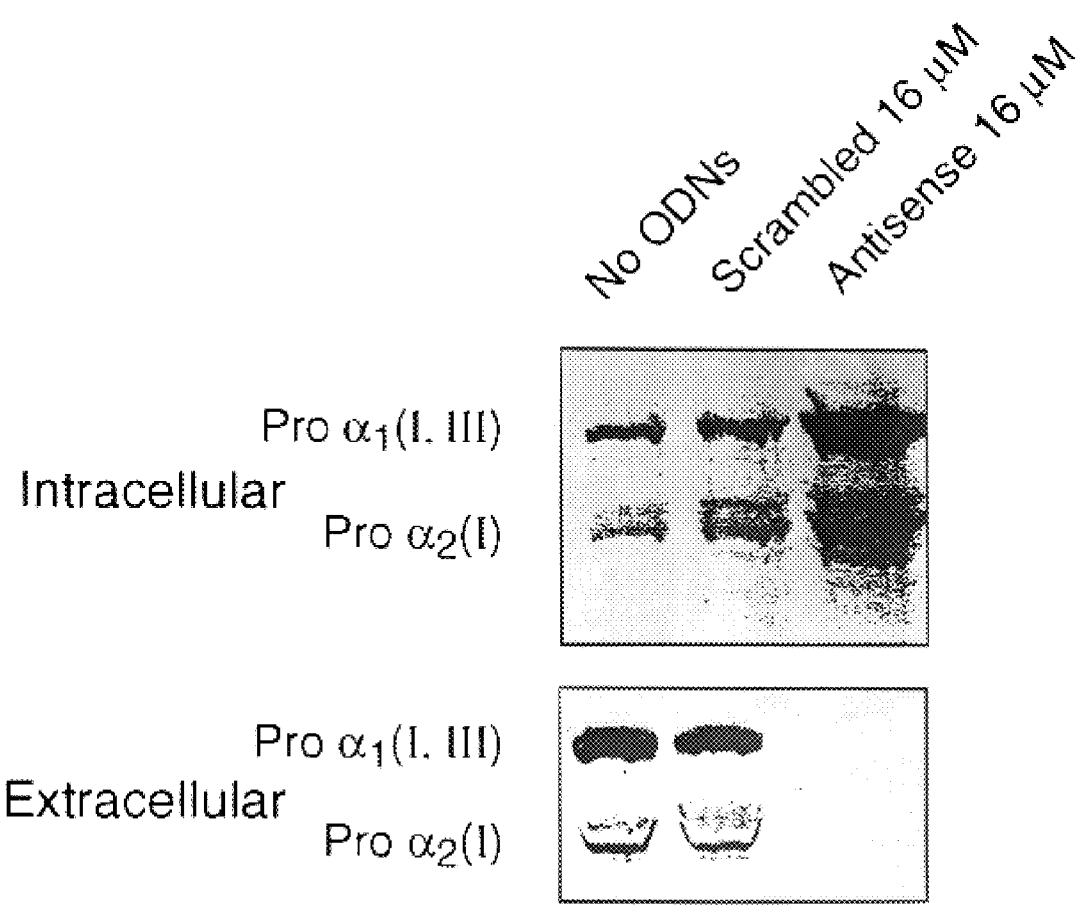

FIG. 10 describes the extracellular and intracellular [$^{14}$C] proline labeled proteins. Cells were incubated with or without oligonucleotides for 16 hours, then labeled with [$^{14}$C] proline for an additional 4 hours in serum-free medium. [$^4$C]proline labeled proteins were analyzed on polyacrylamide SDS gels. The inhibition of radiolabeled proteins in conditioned media was seen which was accompanied by an increased level of intracellular procollagen $\alpha_1$(I) and $\alpha_2$(I) following c-myc antisense treatment.

Figure 11:
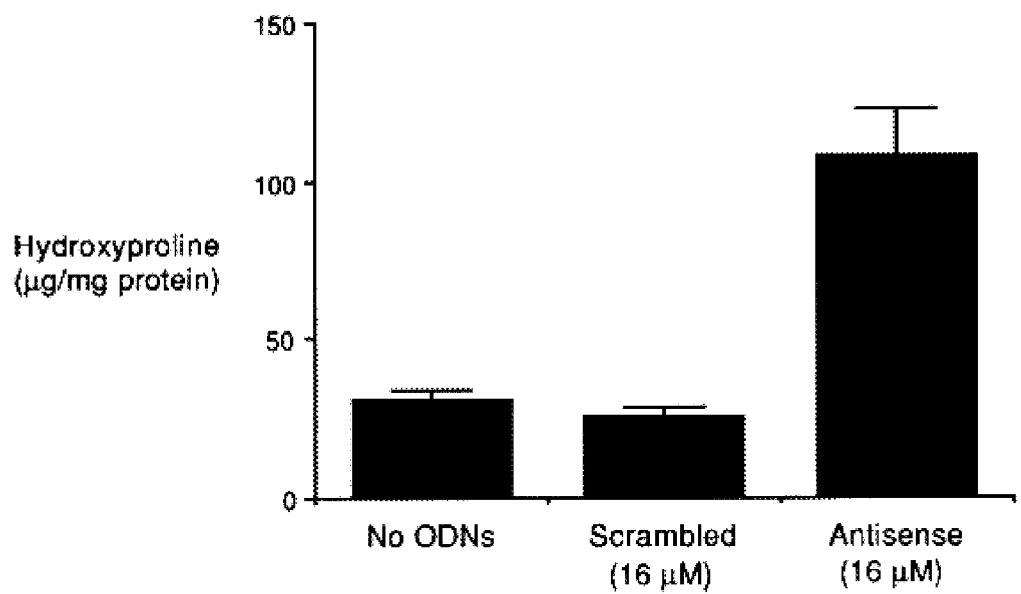

FIG. 11 describes the hydroxyproline content in antisense treated and control human smooth muscle cells.

Figure 12:
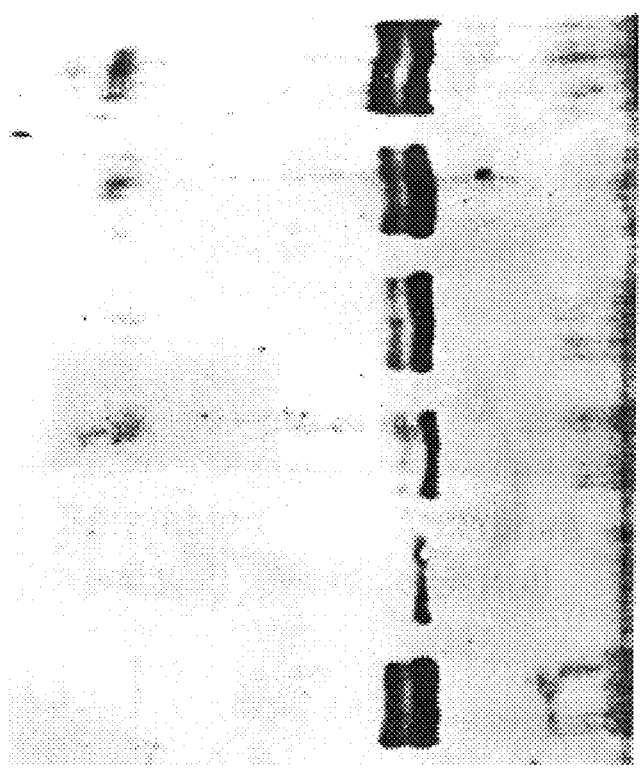

FIG. 12 describes the effect of c-myc antisense treatment on extracellular collagen levels in human skin fibroblasts.

Figure 13:
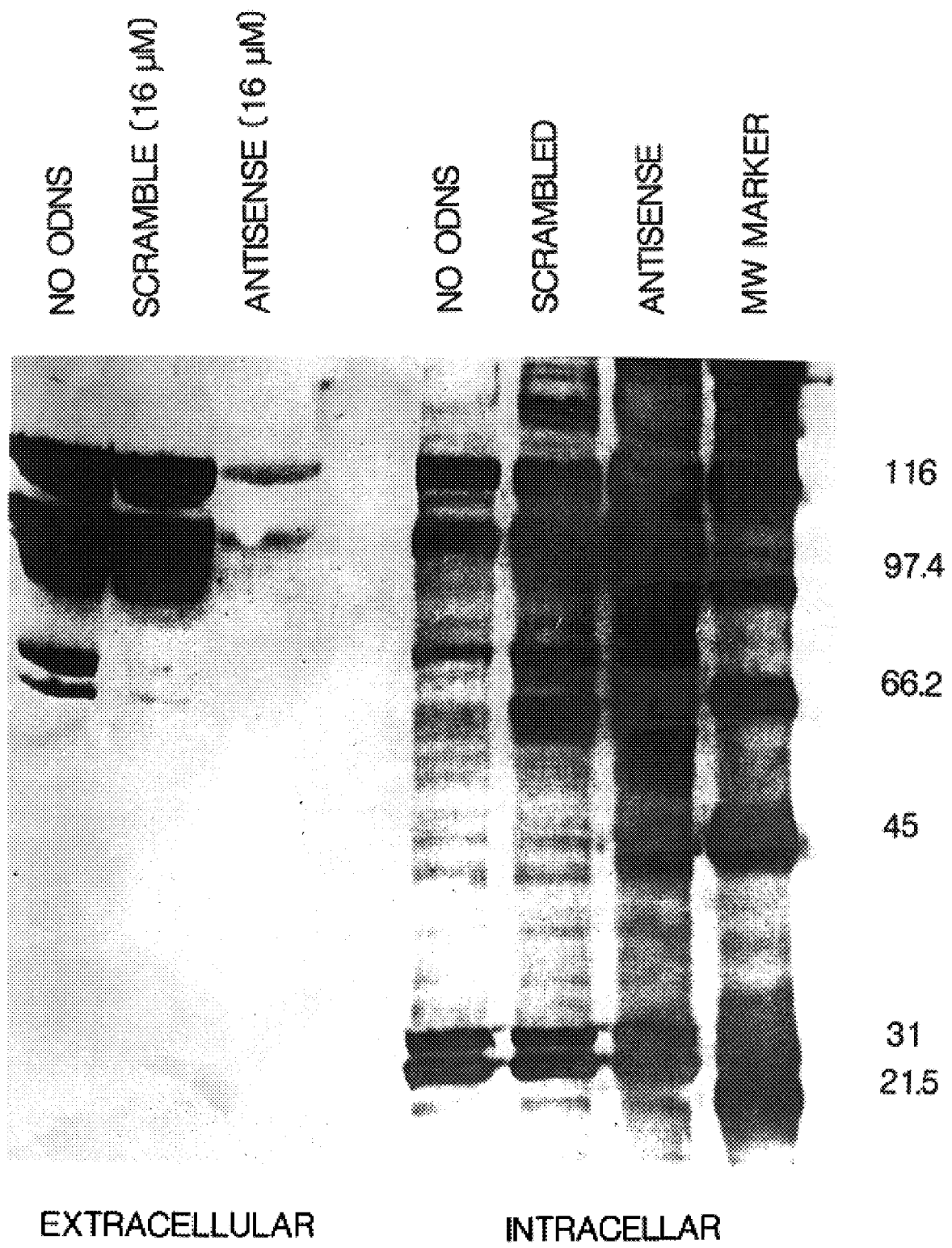

FIG. 13 describes the intracellular and extracellular procollagen level associated with c-myc antisense treated and control human skin fibrolasts.

Figure 14:
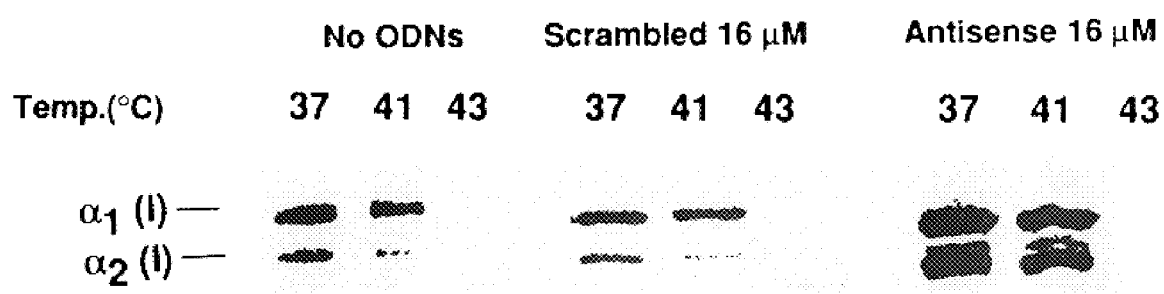

FIG. 14 describes the thermal stability of intracellular procollagen in human skin fibroblasts. The pepsin-purified procollagen from cells treated with or without oligonucleotides was incubated with trypsin and chymotrypsin at indicated temperatures for 2 minutes and electrophoresed on polyacrylamide SDS gels. A similar melting temperature (i.e, about 41° C.) was seen regardless of treatment suggesting a normal triple helical conformation of procollagen $\alpha$ chains after c-myc antisense oligonucleotides.

Figure 15:
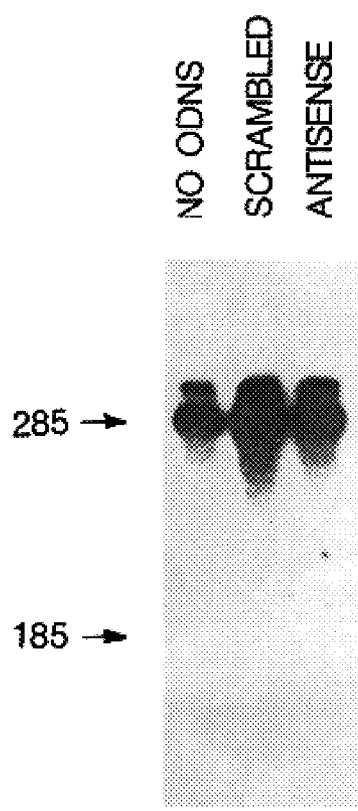

FIG. 15 describes the procollagen $\alpha_1$ (I) mRNA level in c-myc antisense oligonucleotide treated and control human skin fibroblasts.

Figure 16:
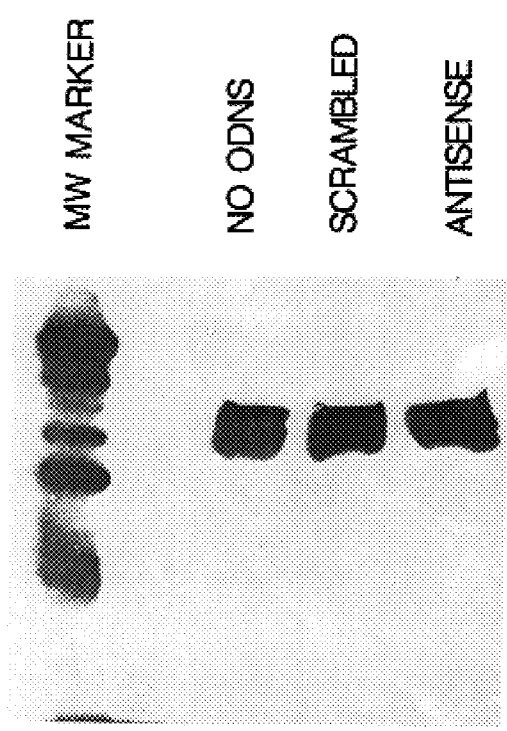

FIG. 16 describes the collagen I levels in c-myc antisense treated and control human skin fibroblast 24 hours after treatment with oligonucleotides.

Figure 17:
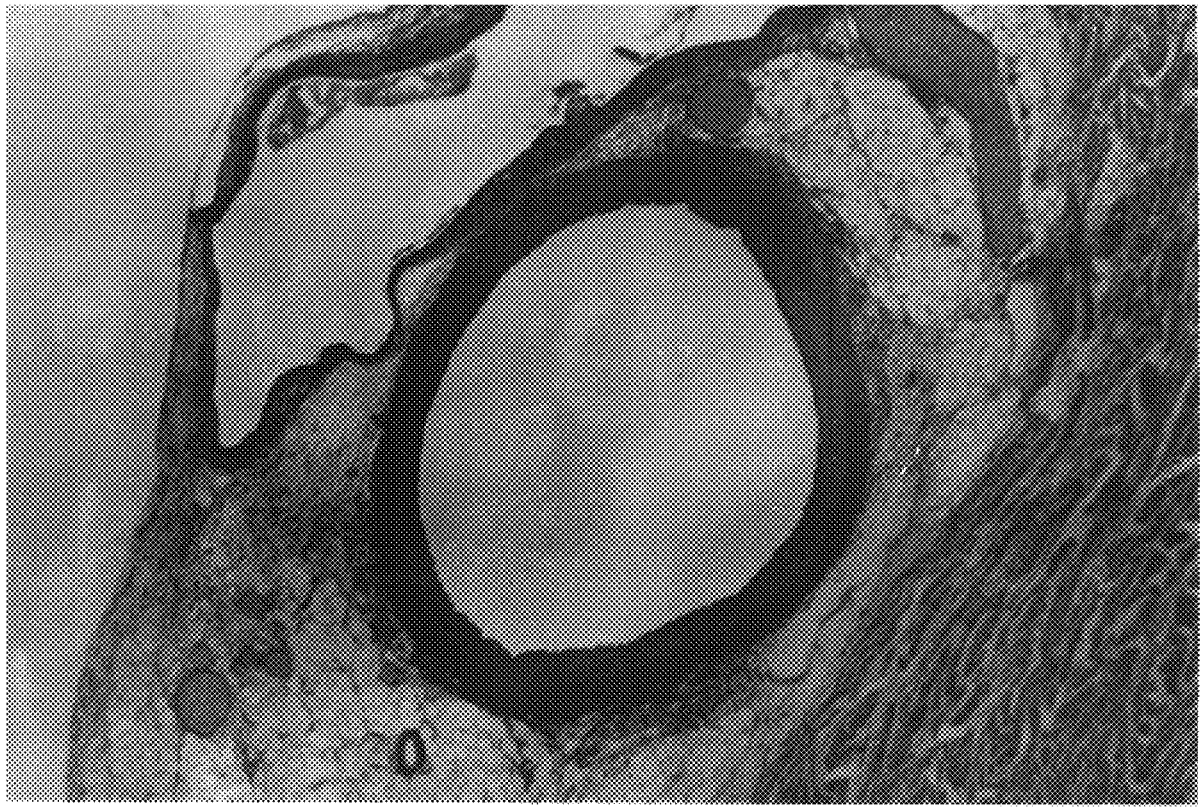

FIG. 17 describes a cross-sectional view of a porcine coronary artery and perivascular tissues. Distribution of c-myc antisense oligonucleotides (Seq. ID NO:1) was assessed within the vessel wall and in the adjacent perivascular tissues. (Magnification×20).

FIGS. 18A–F describe the patterns of c-myc antisense (SEQ. ID NO:1) ODN distribution in the coronary arteries 30 minutes following transcatheter administration. Panels A and B: Phase-contrast and fluorescence microscopy photomicrographs of the same section demonstrating transmural localization of fluorescein-labeled oligonucleotides. Antisense oligonucleotides are present in the media, adventitia and perivascular tissues. Panels C and D: Phase-contrast and fluorescence microscopy photomicrographs showing subintimal, non-transmural ODN distribution. oligonucleotides are detectable only in the media. Panels E and F.: Phase-contrast and fluorescence microscopy photomicrographs exhibiting midwall, non-transmural ODN presence. (Magnification×62.5).

Figure 19A:
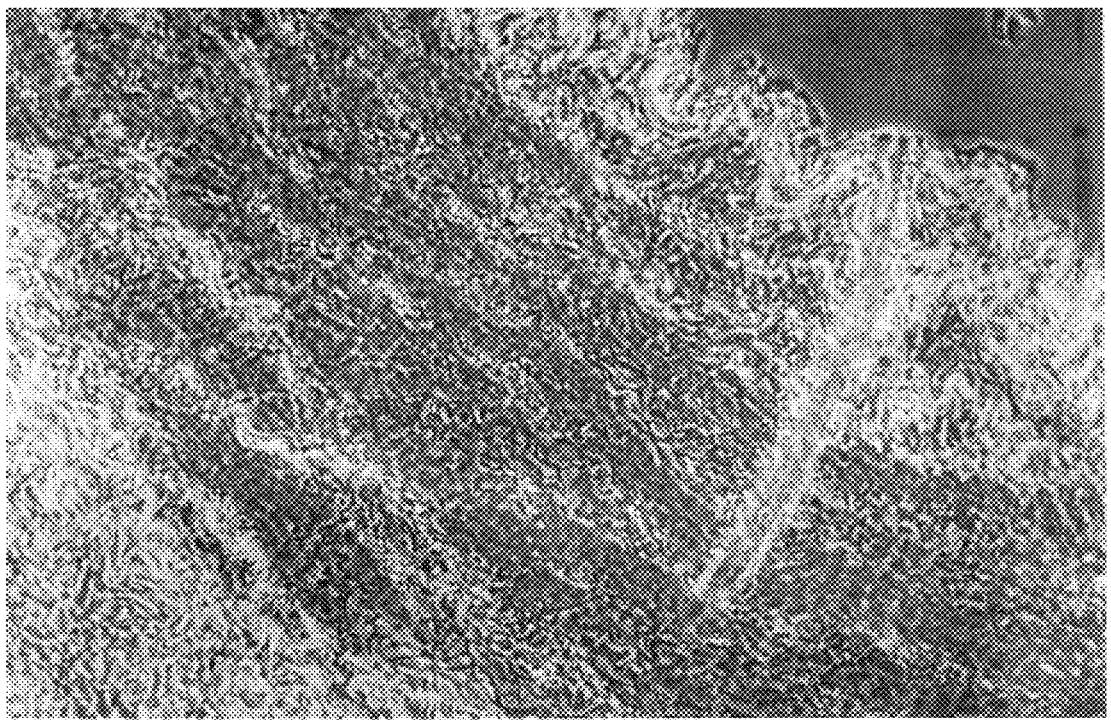

FIGS. 19A and B describe the persistence of c-myc antisense oligonucleotides within the arterial wall 3 days following transcatheter administration. Panels A and B: Phase-contrast and fluorescence microscopy photomicrographs of the same section respectively. (Magnification× 62.5).

Figure 20:
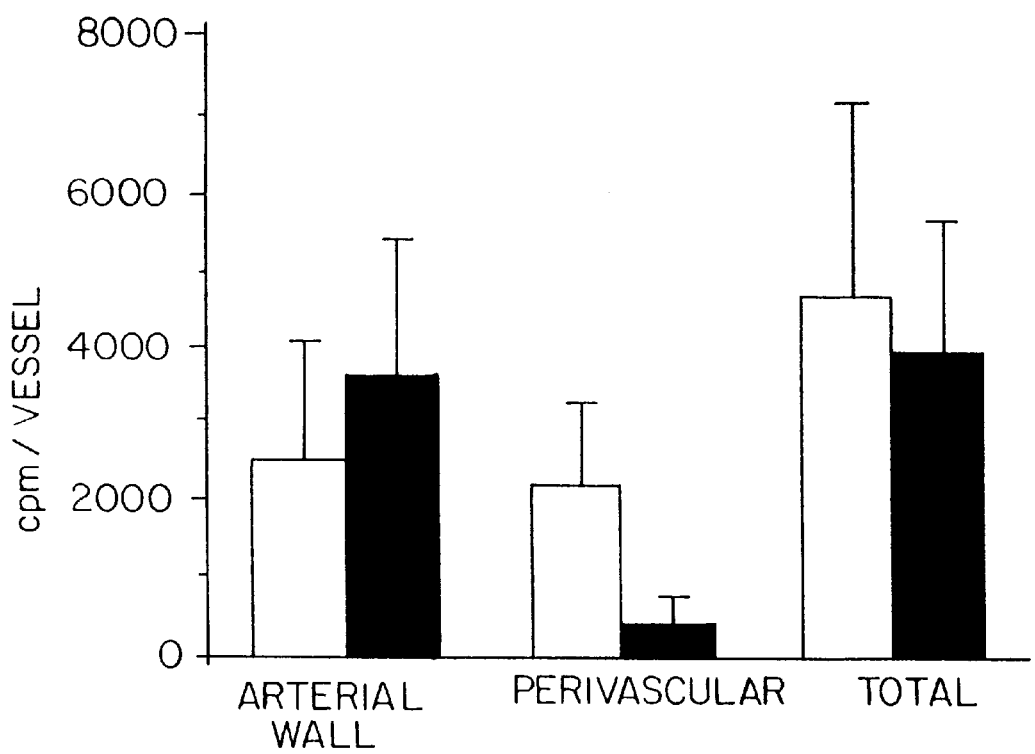

FIG. 20 describes a bar graph depicting vessel-associated and perivascular radioactivities following intramural administration of $^{35}$S-labeled phosphorothioate c-myc antisense oligonucleotides. A similar total ODN content is noted at 30 min (n=6) and at 3 days (n=4) after their delivery due to ODN trafficking from the perivascular space toward the vessel wall. Results are presented as mean±SEM.

FIGS. 21A–D describe the presentation of vascular structures following transcatheter administration of c-myc antisense oligonucleotides. Panel A: fluorescence-labeled oligonucleotides are clearly visible within the coronary aerial wall at 30 minutes after injection. Panel B: adjacent sections demonstrate preserved internal elastic lamina and normal orientation of elastic tissues without disruption (Verhoeff stain). Panel C: mild decrease of cytoplasmic staining and nuclear pyknosis was noted at the site of ODN retention (hematoxylin and eosin stain). Panel D: section adjacent to shown in FIG. 19 demonstrating resolution of the above changes 3 days after delivery of oligonucleotides (hematoxylin and eosin stain, magnification×50).

Figure 22:
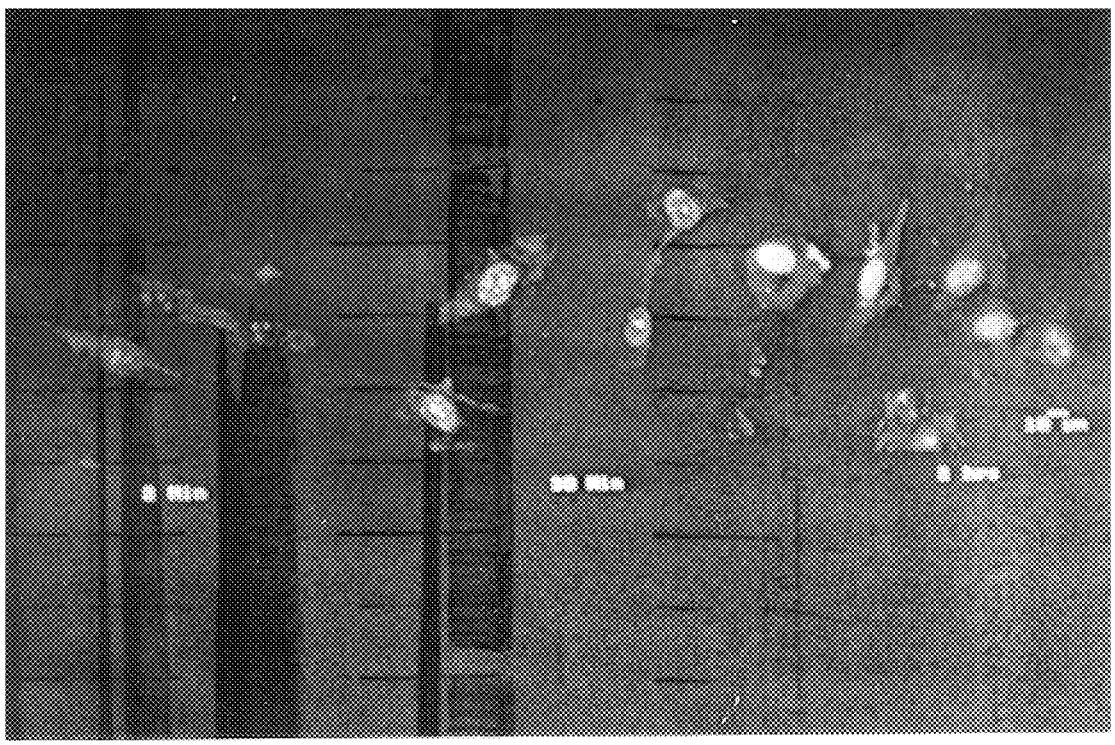

FIG. 22 describes the intracellular localization of fluorescein-labeled c-myc antisense oligonucleotides assessed by confocal microscopy of vascular smooth muscle cells in vitro.

Figure 23:
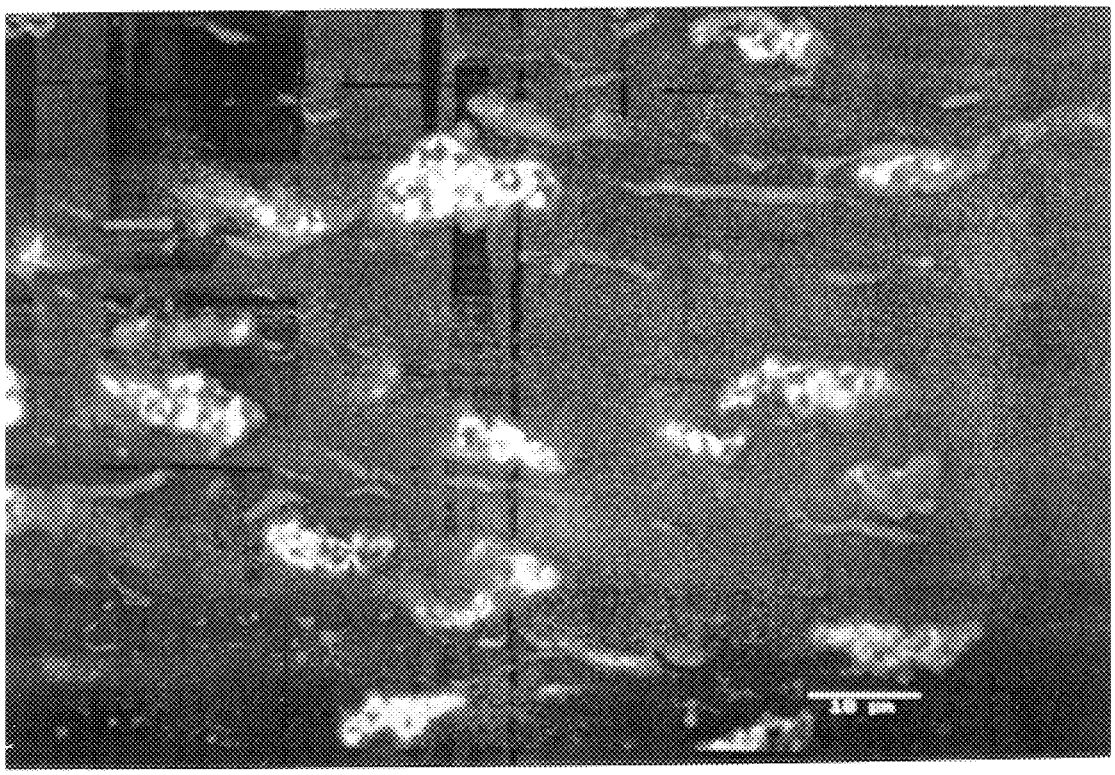

FIG. 23 describes the intracellular localization of fluorescein-label c-myc antisense oligonucleotides 30 minutes after intramural delivery of oligonucleotides in vivo, nuclear localization is visible in medial smooth muscle cells.

Figure 24:
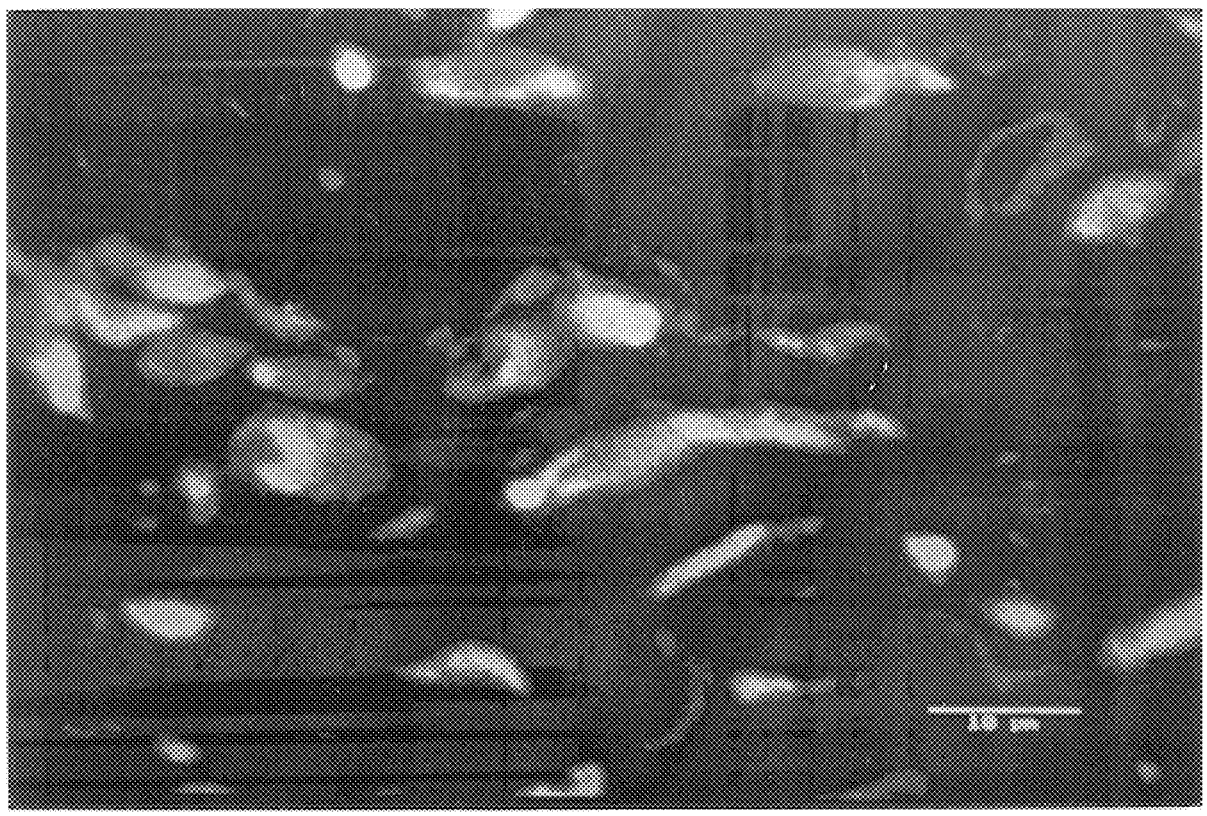

FIG. 24 describes the intracellular localization of fluorescein-label c-myc antisense oligonucleotides 30 minutes after intramural delivery of oligonucleotides in vivo, nuclear localization is visible in adventitial smooth muscle cells.

DEFINITIONS

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilothioate, phosphoranilidate, phosphoramidate, and the like, as more fully described below.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. duplex or triplex stability, specificity, or the like.

"Stability" in reference to duplex or triplex formation roughly means how tightly an antisense oligonucleotide binds to its intended target sequence; more precisely, it means the free energy of formation of the duplex or triplex under physiological conditions. Melting temperature under a standard set of conditions, e.g. as described below, is a convenient measure of duplex and/or triplex stability. Preferably, antisense oligonucleotides of the invention are selected that have melting temperatures of at least 50° C. under the standard conditions set forth below; thus, under physiological conditions and the preferred concentrations duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, antisense oligonucleotides of the invention form perfectly matched duplexes and/or triplexes with their target polynucleotides.

The term "synthesis" as used herein in a biological context refers to a process involved in the production of biological molecules, in particular extracellular matrix molecules and extracellular matrix proteins. The term "synthesis" includes processes both inside and outside a cell that result in biological molecules, for example, but not limited to, mRNA transcription, mRNA translation, post-translational protein modification, glycosylation, peptidase cleavage, extracellular peptidase cleavage, intra-cellular peptidase cleavage, protein transport, protein secretion and protein phosphorylation. Preferably the invention inhibits protein translation of extracellular matrix molecules, post-translational protein processing, protein secretion or intracellular peptidase cleavage.

The term "collagen" as used herein refers to a class of molecules which are synthesized from procollagen. Collagen is synthesized from procollagen extracellularly, by the cleavage of N- and C-termini outside the cell. Antibodies to the triple helical region of collagen can recognize the triple helical region in procollagen as well. Antibodies used herein are either specific for collagen I and procollagen I or collagen III and procollagen III. Collagen can also be synthesized in vitro from procollagen by pepsin.

DETAILED DESCRIPTION OF THE INVENTION

The invention relates to the use of certain antisense compounds to inhibit the inappropriate synthesis in a tissue of extracellular matrix proteins, particularly collagen, and more particularly type I and type III collagen. The inappropriate and/or excessive synthesis of extracellular matrix proteins can result in medical conditions that exhibit formation of, e.g., unwanted fibrous connective tissue. Such medical conditions include sclerotic disorders, vascular restenosis, atherosclerosis, atherogenesis, keloid disease, liver cirrhosis, rheumatoid disorders of the joints, post-surgical scarring, reconstructive surgery, and the like, generally found in human subjects. A range of tissue types can be the site of such inappropriate synthesis, including vascular smooth muscle cells, endothelial cells, skin and organ fibroblasts, e.g. in keloid disease or posttraumatic or post-surgical scar formation, and synovial cells and other joint components. The invention is particularly useful in the treatment of restenosis, an acute vascular injury, typically following angioplasty in a human subject. Restenosis is associated with smooth muscle cell migration to the vascular intima, proliferation, and synthesis of extracellular matrix components, e.g. Holmes et al, Chapter 12 in Vlietstra et al, Editors, PTCA (Davis Company, Philadelphia, 1987).

By administering a therapeutically effective amount of an antisense compound to a tissue having a target polynucleotide the inappropriate (i.e. excessive) synthesis of extracellular protein is inhibited. Target polynucleotides may be single stranded or double stranded DNA or RNA; however, single stranded DNA or RNA targets are preferred. The genomic nucleotide sequence and the mRNA transcripts of nuclear oncogenes of the invention are known in the art and include c-myc, c-myb, c-fos, N-myc, L-myc, p53, c-rel, c-ski, c-ets-1, c-ets-2, and the like, e.g. Glover, editor, Oncogenes (IRL Press, Oxford, 1989). More particularly, c-myc and c-myb sequences are described in the following references: c-myc proto-oncogene sequences are described in Marcu et al, Ann. Rev. Biochem., 61:809–860 (1992); Watt et al, Nature, 303:725–728 (1983); Battey et al, Cell, 34:779–787 (1983); and Epstein et al, NTIS publication PB93–100576; the c-myb proto-oncogene is described in Gewirtz et al, U.S. Pat. No. 5,098,890 and Majello et al, Proc. Natl. Acad. Sci. 79:9636–9640 (1986). Preferably, the nuclear proto-oncogenes targeted by antisense oligonucleotides of the invention are c-myc and/or c-myb.

It is understood that the target to which the c-myc antisense oligonucleotides of the invention are directed include allelic forms of the proto-oncogenes. There is substantial guidance in the literature for selecting particular sequences for antisense oligonucleotides given a knowledge of the sequence of the target polynucleotide, e.g. Ulmann et al (cited above); Crooke (cited above); and Zamecnik and Stephenson, Proc. Natl. Acad. Sci, 75: 280–284 (1974). Preferably, the sequences of c-myc antisense compounds are selected so that the G-C content is at least 60%. Preferred mRNA targets include the 5' cap site, tRNA primer binding site, the initiation codon site, the mRNA donor splice site, the mRNA acceptor splice site, and the like, e.g. Goodchild et al, U.S. Pat. No. 4,806,463.

When selecting antisense oligonucleotides to target the ATG intiation site of human c-myc in the second exon, antisense oligonculeotide with consecutive sequences can be administered using oligonculeotides 12, 13, 14, 15, 16, 17, 18, 19, 20, 21, 22, 23, 24, 25, 26, 27, 28, 29, 30, 31, 32, 33, 34, or 35 bases in length and selected from a twenty five base region on either side of the ATG site (sequence from Gazin et al,):

5' cccgc tccagcagcc tcccgcgacg ATG cccctcaacg ttagct- tcac caaca 3' Preferably antisense oligonucleoitdes will include the ATG site. Twenty five base regions on either side of SEQ. ID. NO: 6 and 7 may be also be used to select oligonucleotides of the size discussed in this paragraph.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention may also contain pendent groups or moieties, either as part of or separate from the basic repeat unit of the polymer, to enhance specificity, nuclease resistance, delivery, or other property related to efficacy, e.g. cholesterol moieties, duplex intercalators such as acridine, poly-L-lysine, "end capping" with one or more nuclease-resistant linkage groups such as phosphorothioate, and the like. Sequences of certain representative oligonucleotides useful in this invention are set forth in the Sequence Listing included herewith.

Antisense compounds of the invention include the pharmaceutically acceptable salts thereof, including those of alkaline earths, e.g. sodium or magnesium, ammonium or $NX_4^+$, wherein X is $C_1$–$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

Preferably, nuclease resistance is conferred on the antisense compounds of the invention by providing nuclease-resistant internucleosidic linkages. Many such linkages are known in the art, e.g. phosphorothioate: Zon and Geiser, Anti-Cancer Drug Design, 6: 539–568 (1991); Stec et al, U.S. Pat. No. 5,151,510; Hirschbein, U.S. Pat. No. 5,166, 387; Bergot, U.S. Pat. No. 5,183,885; phosphorodithioates: Marshall et al, Science, 259:1564–1570 (1993); Carathers and Nielsen, International application PCT/US89102293; phosphoramidates, e. g. —OP(=O)($NR^1IR^2$)—O— with $R^1$ and $R^2$ hydrogen or $C_1$–$C_3$ alkyl: Jager et al, Biochemistry, 27:7237–7246 (1988); Froehler et al, International application PCT/US90/03138; peptide nucleic acids: Nielsen et al, Anti-cancer Drug Design, 8: 53–63 (1993), International application PCT/EP92/01220; methylphosphonates: Miller et al, U.S. Pat. No. 4,507,433, Ts'o et al, U.S. Pat. No. 4,469,863, Miller et al, U.S. Pat. No. 4,757,055; and P-chiral linkages of various types, especially phosphorothioates, Stec et al, European patent application 92301950.9 and Lesnikowski, Bioorganic Chemistry, 21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl ($C_1$–$C_6$)- or diphenylsilyl, sulfamate ester, and the like. Such linkages and methods for introducing them into oligonucleotides are described in many references, e.g. reviewed generally by Peyman and Ulmann (cited above); Milligan et al (cited above); Matteucci et al, International application PCT/US91/06855. Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage. It is understood that in addition to the preferred linkage groups, compounds of the invention may comprise additional modifications, e.g. boronated bases, Spielvogel et al, 5,130,302; cholesterol moieties, Shea et al, Nucleic Acids Research, 18:3777–3783 (1990) or Letsinger et al, Proc. Natl. Acad. Sci., 86:6553–6556 (1989); 5-propenyl modification of pyrimidines, Froehler et al, Tetrahedron Lett., 33: 5307–5310 (1992); and the like.

Preferably, antisense compounds of the invention are synthesized by conventional means on commercially available automated DNA synthesizers, e.g. an Applied Biosystems (Foster City, Calif.) model 380B, 392 or 394 DNA/RNA synthesizer. Preferably, phosphoramidite chemistry is employed, e.g. as disclosed in the following references: Beaucage and Iyer, Tetrahedron, 48:2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88:9397–9401 (1991); Roberts et al, Science, 258:1463–1466 (1992); Distefano et al, Proc. Natl. Acad. Sci., 90:1179–1183 (1993); Mergny et al, Biochemistry, 30:9791–9798 (1991); Cheng et al, I. Am. Chem. Soc., 114:4465–4474 (1992); Beal and Dervan, Nucleic Acids Research, 20:2773–2776 (1992); Beal and Dervan, 1. Am. Chem. Soc., 114:4976–4982 (1992); Giovannangeli et al, Proc. Natl. Acad. Sci., 89: 8631–8635 (1992); Moser and Dervan, Science, 238:645–650 (1987); McShan et al, J. Biol. Chem., 267:5712–5721 (1992); Yoon et al, Proc. Natl. Acad. Sci., 89:3840–3844 (1992); Blume et al, Nucleic Acids Research, 20:1777–1784 (1992); and the like.

The length of the oligonucleotide moieties is sufficiently large to ensure that specific binding will take place only at the desired target polynucleotide and not at other fortuitous sites, as explained in many references, e.g. Rosenberg et al, International application PCT/US92105305; or Szostak et al, Meth. Enzymol. 68:419–429 (1979). The upper range of the length is determined by several factors, including the inconvenience and expense of synthesizing and purifying oligomers greater than about 3040 nucleotides in length, the greater tolerance of longer oligonucleotides for mismatches than shorter oligonucleotides, whether modifications to enhance binding or specificity are present, whether duplex or triplex binding is desired, and the like. Usually, antisense compounds of the invention have lengths in the range of about 12 to 60 nucleotides. More preferably, antisense compounds of the invention have lengths in the range of about 15 to 40 nucleotides; and most preferably, they have lengths in the range of about 18 to 30 nucleotides.

Preferably, the thermal stability of the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 $\mu$M. Typical conditions are as follows: 150 mM NaCl and 10 mM $MgCl_2$ in a 10 mM sodium phosphate buffer (pH 7.0) or in a 10 mM Tris-HCl buffer (pH 7.0); or like conditions. Data for melting curves are accumulated by heating a sample of the antisense oligonucleotide/target polynucleotide complex from room temperature to about 85–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UVIVIS spectrophotometer and model HP 89100A temperature controller, or like instruments. Such techniques provide a convenient means for measuring and comparing the binding strengths of antisense oligonucleotides of different lengths and compositions.

Another aspect of this invention is a pharmaceutical composition useful inhibiting the synthesis of extracellular matrix proteins, comprising a pharmaceutically-acceptable excipient and an antisense oligonucleotide specific for nuclear proto-oncogene that is present in an amount sufficient to inhibit the synthesis of extracellular matrix proteins when administered to a subject in need thereof. Thus, the antisense oligonucleotides of the invention are employed as one or more components of such a pharmaceutical composition. Components of pharmaceutical compositions of the invention depend on several factors, including the nature of the disease or condition being treated, the location of disease lesions, the mode of drug delivery and/or administration contemplated, the latter of which can include in vivo administration by way of a catheter into a target lesion or organ, topical application, intranasal administration, administration by implanted or transdermal sustained release systems, and the like.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. For formulations containing weakly soluble antisense compounds, microemulsions may be employed, for example by using a nonionic surfactant such as Tween 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

Sustained release systems suitable for use with the pharmaceutical compositions of the invention include semipermeable polymer matrices in the form of films, microcapsules, or the like, comprising polylactides, copolymers of L-glutamic acid and gamma-ethyl-L-glutamate, poly(2-hydroxyethyl methacrylate), and like materials, e.g. Rosenberg et al, International application PCT/US92/05305. Sustained release systems also include liposomally entrapped antisense compounds, e.g. as described in Liposome Technology, Vol. II, Incorporation of Drugs, Proteins, an Genetic Material (CRC Press).

An effective amount of c-myc antisense oligonucleotide for particular applications depends on several factors, including the chemical nature of the antisense oligonucleotide, the disorder being treated, the method of administration, and the like. Preferably, an effective amount will provide a concentration of c-myc antisense oligonucleotide of between about 1 to 100 $\mu$M at the target polynucleotide; and more preferably, an effective amount will provide a concentration of antisense oligonucleotide of between about 1 to 10 $\mu$M at the target polynucleotide.

For vascular disorders, such as restenosis, antisense oligonucleotides specific for nuclear proto-oncogenes are preferably administered locally to the traumatized artery by way of a catheter. Preferably, the antisense oligonucleotides delivered to restenosis lesion are specific for c-myc and/or c-myb; more preferably, a combination of antisense oligonucleotides specific for both c-myc and c-myb is employed to reduce extracellular matrix protein synthesis associated with restenosis. Typically, restenosis occurs after a procedure such as percutaneous transluminal coronary angioplasty (PTCA) which causes a local disruption or injury to an arterial wall. In response to such injury, an occlusive lesion frequently results from the following phenomena: inflammation of the of the artery at the injury site, thrombosis, the accumulation of smooth muscles cells by migration and proliferation, and the synthesis of extracellular matrix.

For intravascular application (e.g. to prevent restenosis after angioplasty) antisense oligonucleotides are preferably administered in the vicinity of the lesion via catheter from inside the lumen, or through the adventitia (i.e. the most outer layer of the vessel wall) with materials aiding a slow release of antisense compound, e.g. a pluronic gel system as described by Simons et al, Nature, 359:67–70 (1992) or porous balloon or iontophoretic balloon as described by Fernandez-Ortiz, A., et al., Circulation, 89:1518–1522 (1994), the methods of which are incorporated by reference herein. Other slow release techniques for local delivery include coated stents with antisense compound, e.g. using a binder or gel, described in Wilensky et al, Trends in Cardiovascular Med., 3: 163–170 (1993). A dose delivered at the target lesion is in the range of from 1 µg to 10 mg for each or both of the antisense compounds employed in the pharmaceutical composition. Preferably the dose range is between 1 µg and 1 mg; and more preferably, the dose range is between 1 µg and 10 µg. Preferably, the delivery time is in the range of about 30 seconds to 60 minutes, and more preferably, in the range of about 30 seconds to about 1–2 minutes, e.g. Zalewski et al, pages 79–87 in Goldberg, editor, Coronary Angioplasty (Davis, Philadelphia, 1988).

For catheter administration the administered dose is in the range of 0.1 mg to 10 mg per artery, preferably 0.25 mg to 4 mg per artery and more preferably 0.5 mg to 2 mg per artery. Administered dose is the amount drug applied to the tissue, where as "dose delivered at the target lesion" is in the amount of drug in the tissue after delivery to the tissue.

The techniques of coronary angioplasty are well known to those skilled in the art and are described in detail in such comprehensive treatises as Clark, Coronary Angioplasty (Liss, New York, 1987), Vlietstra et al (cited above), and the like.

For excessive scar formation in the skin, e.g. postsurgical scars, keloid disease, or the like, topical or intradermal application is preferred to inhibit extracellular matrix protein synthesis, particularly collagen synthesis, by skin fibroblasts.

For topical application the administered dose (amount of drug applied to tissue) will generally range from 0.01 µg to 10 mg of drug per cm$^2$, preferably from 0.2 µg to 7 mg of drug per cm$^2$, and more preferably from 0.5 to 4 mg of drug per cm$^2$. Administered dose for use with post-surgical dressing is preferably from 0.2 mg to 4 mg of drug per cm$^2$. The administered dose for use with topical creams for skin abrasions, skin lesions, acne and post-surgical treatments is preferably from 0.05 mg to 3 mg of drug per cm$^2$.

For urologic disorders resulting in urethral, ureteral, or bladder scarring or narrowing, local administration via catheter or implants coated with antisense oligonucleotide is preferred.

For excessive scarring of internal organs containing smooth muscle cells and fibroblasts, such as gastrointestinal organs, biliary ducts, lungs, and liver, administration of antisense compounds can be systemic or local. Local administration includes direct injection of antisense oligonucleotides into the target organ, delivery via implanted gels or polymers, or slow release from coated stents or other prosthetic materials.

For each of the disorders described above, criteria for selecting patients for treatment and means for assessing therapeutic endpoints are well known in the art concerning the specific disorders. For example, in regard to vascular restenosis factors associated with susceptibility to the condition include male gender, dilation for stenosis of bypass grafts, Canadian Heart class 3 or 4 at baseline, and history of myocardial infarction, Holmes et al, Chapter 12 in Vlietstra et al, editors, PTCA (Davis Company, Philadelphia, 1987). Efficacy of treatment is assessed in the same manner as in any PTCA technique. Usually, results are estimated visually, but other techniques are available. Assessment of the severity of a stenosis, or restenosis (for determining a candidate for PTCA or the results of PTCA) range from visual observation of the lesion to complex computer-based analysis of the dimensions of the artery in question, e.g. from tomographical data, flow in the distal vascular bed, densitometric characteristic of the stenosis, or regional wall motion changes in the zone of the lesion, e.g. Bove, Chapter 9 in Vlietstra et al (cited above).

Example I

Inhibition of Collagen Synthesis in Human Smooth Muscles Cells

In this example, explanted human smooth muscle cells committed to collagen synthesis were treated with c-myc or c-myb antisense oligonucleotide and compared with untreated and/or "sense" treated controls.

Human smooth muscles cells (SMCs) originated from the saphenous veins of patients undergoing routine bypass surgery. The cells were isolated by an explant method. The explants were placed into tissue culture dishes containing Dulbecco's modified Eagle's medium (DMEM) supplemented with 20% heat inactivated fetal bovine serum (FBS), 100 IU/ml penicillin, 100 µg/ml streptomycin, and 2 mM/ml glutamine (CM-20). The cultures were maintained at 37° C. in a humidified incubator with 5% $CO_2$. The cells exhibited typical morphological characteristics of vascular smooth muscle cells i.e., spindle shape and hill-and-valley pattern. The identification of vascular smooth muscle cells was further confirmed by in situ smooth muscle β-actin staining. Cells were grown to confluence and subcultured every 7 days. Only 3rd or 4th passage human smooth muscle cells were used for experiments.

The experiments were carried out in subconfluent and post confluent human smooth muscle cells. Cells were plated at 10,000/cm$^2$ (subconfluent) or 25,000/cm$^2$ (post confluent) supplemented with CM-20. Three days after plating, fresh CM-20 containing ascorbic acid (50 µg/ml) was added. The following oligonucleotides were added (16 µM) to the cultures in the various experiments:

antisense (5'-AACGTTGAGG GGCAT)(SEQ ID NO: 1);
sense oligomers (5'-ATGCCCCTCA ACGTT)(SEQ ID NO: 2);
4 bp mismatch oligomer (5'AACGTGGATT GGCAG)(SEQ ID NO: 3);
scrambled oligomer (5'-GAACGGAGAC GGTTT)(SEQ ID NO: 4);
or c-myb antisense (5'-TATGCTGTGC CGGGGTCTTC GGGC)(SEQ ID NO: 5).

Twenty four hours later, the culture medium was collected for Western blots and the cells were harvested for RNA analysis. A trypan blue exclusion assay was carried out with each experiment.

Collagen was measured as follows: Both pepsin treated (triple helical portion of collagen I) or non-pepsin treated samples were subjected to Western blot for collagen measurement. Briefly, the samples were incubated at 4° C. overnight in pepsin (1 mg/ml) and acetic acid (0.5 mol). Equal volume aliquots of samples were then concentrated in a speed vacuum centrifuge, after which samples were dissolved in SDS gel loading buffer (50 mM tris • HCl pH 6.8, 100 mM dithiothreitol, 2% SDS, 0.1% bromophenol blue and 10% glycerol) and boiled for 10 min. Following centrifugation at 11,000 g for 10 min., samples. were electrophoresed through 7.5% SDS-polyacrylamide gel and transferred to nitrocellulose filter. After incubation in blocking solution, the sample-containing filters were incubated with biotin labeled primary antibody against human Collagen I and III (Southern Biotech. SC.) for 1 hour at room temperature. The filters were washed and then incubated with streptavidine labeled with horseradish peroxidase. Following addition of the reaction substrate, the filters were exposed to X ray film. The experiments were repeated at least twice on separate occasions.

Human smooth muscle cells used in all experiments underwent 3–4 passages. The phenotype of these cells is considered to be irreversibly synthetic and is associated with various disease states. It has been demonstrated that abnormal collagen accumulation in the vessel wall was mainly produced by these synthetic cells. Both subconfluent and postconfluent smooth muscle cells produced type I and type III collagens under serum stimulation.

In subconfluent smooth muscle cells, there was 80% reduction in collagen type I synthesis after c-myc antisense oligonucleotide treatment as compared with control (no oligonucleotide added) and c-myc sense oligonucleotide treated cells. In confluent smooth muscle cells, cell numbers counted in the Coulter counter were similar among control, antisense- and sense-treated cells. Viability of cells were 97%, 96% and 95% in the control, antisense- and sense-treated cells using trypan blue exclusion assay. Collagen type I was nondetectable in c-myc antisense-treated cells. Cells treated with c-myc sense oligomer showed no difference in the level of collagen type I protein as compared with control. Triple helical type I collagen was measured after digestion and the results showed the same trends with non-pepsin treated samples.

In subconfluent smooth muscle cells, there was 80% reduction in procollagen type I synthesis after c-myc antisense oligonucleotide (16 $\mu$M) treatment as compared with the control (no oligonucleotide added) and c-myc sense oligonucleotide treatment. In postconfluent smooth muscle cells, collagen type I was nondetectable in c-myc antisense treated cells. Cells treated with sense c-myc oligonucleotides and 4 bp mismatch oligonucleotides showed no reduction in the level of collagen type I protein as compared to the control (no oligonucleotide added). The reduction of collagen type I in both proliferating and postconfluent smooth muscle cells suggests that the inhibition of collagen synthesis is independent of inhibition of cell growth by antisense compounds. Different doses (4, 8, and 16 $\mu$M) of antisense oligonucleotide produced a dose dependent reduction of procollagen type I synthesis. Cell viability following different oligonucleotide treatments was comparable, as analyzed by a trypan blue exclusion assay. More than 90% cells remained viable in all groups.

In postconfluent human smooth muscle cells, the synthesis of collagen type I was abolished by c-myb antisense oligonucleotide at a concentration of 16 $\mu$M. In the control (no oligonucleotide) and cells treated with scrambled sequence oligonucleotides, the level of collagen type I was similar.

Example II

Inhibition of Collagen Synthesis in Human Skin Fibroblast Cells

In this example, explanted human skin fibroblast cells (human FBCs) were treated with c-myc or c-myb antisense oligonucleotide and compared with untreated and/or "sense" treated controls. Human FBCs were obtained from patients undergoing skin transplants and were isolated by an explant method. Explanted FBCs were cultured as described above for human smooth muscle cells and antisense and control oligonucleotides were applied in an identical manner. Human FBCs from 3rd to 10th passage cultures were used in the experiments. Collagen synthesis was measured as described in Example I.

In confluent human FBC, c-myc antisense oligonucleotides (8 and 16 $\mu$M) reduced procollagen type I synthesis in a dose dependent manner. Cells treated with c-myc sense, 4 bp mismatch, or scambled oligonucleotides showed similar levels of collagen type I protein as compared with control cells (no oligonucleotide added).

Example III

Reduction of Neointima Formation in Porcine Model of Coronary Denudation

The effectiveness of c-myc antisense compounds to inhibit neointima formation was tested by administering c-myc-specific antisense (SEQ ID NO: 1) and placebo (SEQ ID NO: 2) oligonucleotide phosphorothioates to the site of coronary angioplasty in a standard porcine model using conventional protocols, e.g. see Karas et al, J. Am. Coll. Card., 20:467–474 (1992); and Schwartz et al, Circulation, 82:2190–2200 (1990). Domestic crossbred pigs (Sus scrofa) were premedicated with oral aspirin (650 mg) prior to the study. General anesthesia consisted of intramuscular injection of ketamine (12 mg/kg) and xylazine (8 mg/kg). Additional doses of anesthesia were given intravenously throughout the experiment. After the right external carotid artery was surgically exposed, heparin (10,000 U) was administered to the pig intravenously, and nifedipine (10 mg) was given buccally. Using an 8 French SAL 1 guiding catheter (Medtronic Interventional Vascular, Inc., Danvers, Mass.) the coronary ostia were cannulated under fluoroscopic guidance. Following intracoronary injection of nitroglycerin (100 $\mu$g), and prior to the delivery of the c-myc antisense and placebo, an oversized angioplasty balloon was used to injure the intimal and medial layers of the arterial walls by inflating at 6–10 atm, according to the size of the artery which varied from 2.0 to 3.5 mm, and holding for 30 seconds three times in succession. Immediately after the angioplasty balloon was removed, intramural injections (1 mg/vessel) to the coronary arteries were carried out using a separate porous balloon. It was predetermined that intramural drug delivery was safe when the injection pressure did not exceed 4 atm, the volume of perfusate was 2 ml, and the balloon-artery ratio was about 1.4 to 1. The c-myc antisense (13 replicates) or placebo (12 replicates) oligomers were injected under 4 atm of pressure and delivery was completed in an average of 27 seconds. The dose of oligomers was 1 mg per injured coronary artery. No adverse effects were associated with the delivery of the oligomers. One month after delivery, the animals were sacrificed and the maximal neointimal area (NA max), the neointimal thickness (NT max), and the residual lumen (RL) at the injury sites were determined by morphometry. The results (mean±SEM) are shown in Table I below:

TABLE I

| Oligomer | Replicates | NA max (mm$^2$) | NT max (mm) | RL (%) |
|---|---|---|---|---|
| placebo | 12 | 0.80 ± 0.17 | 0.48 ± 0.09 | 64 ± 6 |
| antisense | 13 | 0.24 ± 0.06 | 0.20 ± 0.04 | 81 ± 5 |
| p | | <0.01 | <0.01 | <0.05 |

Figure 1:
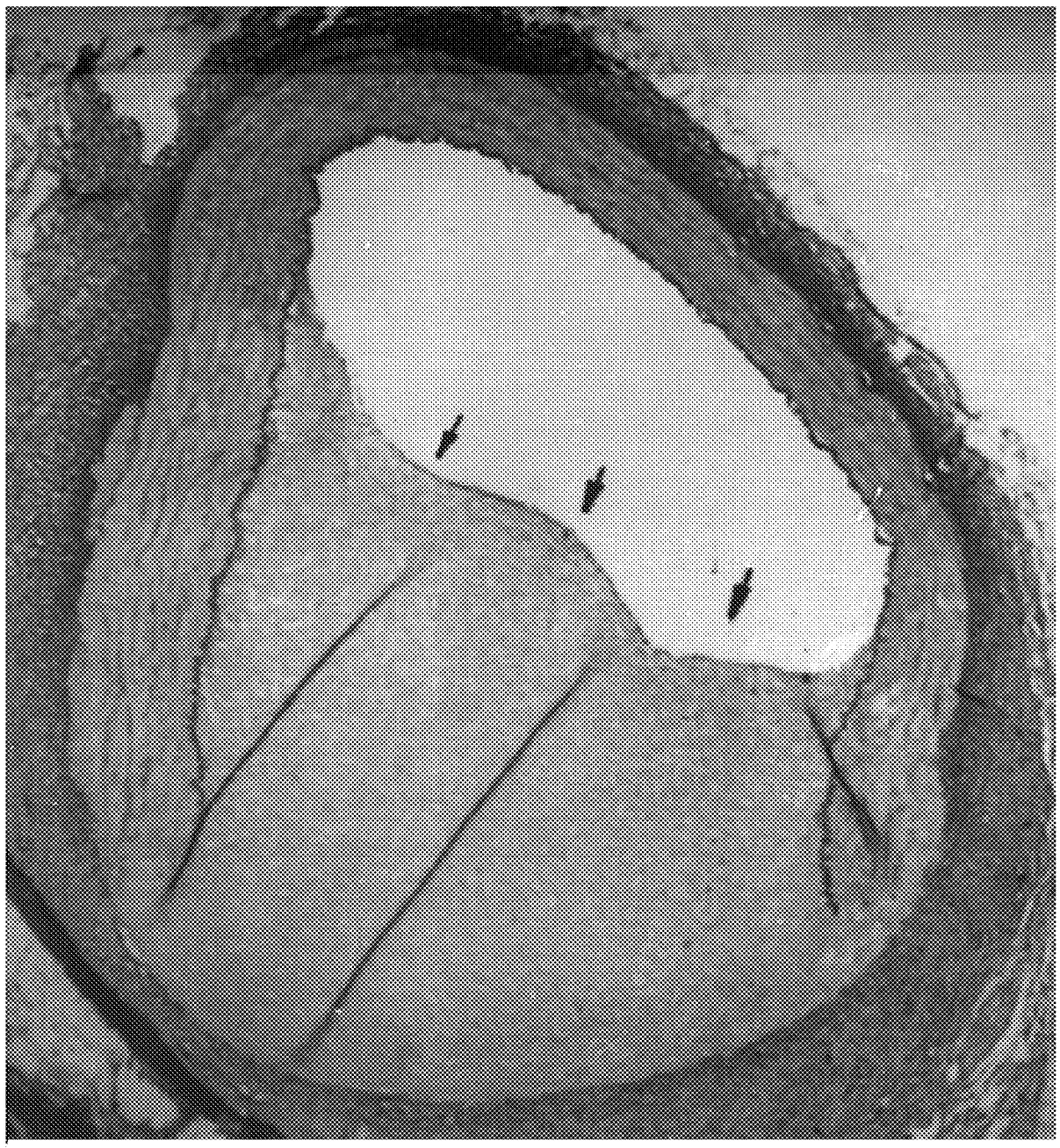
FIG. 1 is a photograph of a cross-section of an exemplary control (i.e., which received sense oligomer injection) coronary artery one month following injury.
Figure 2:
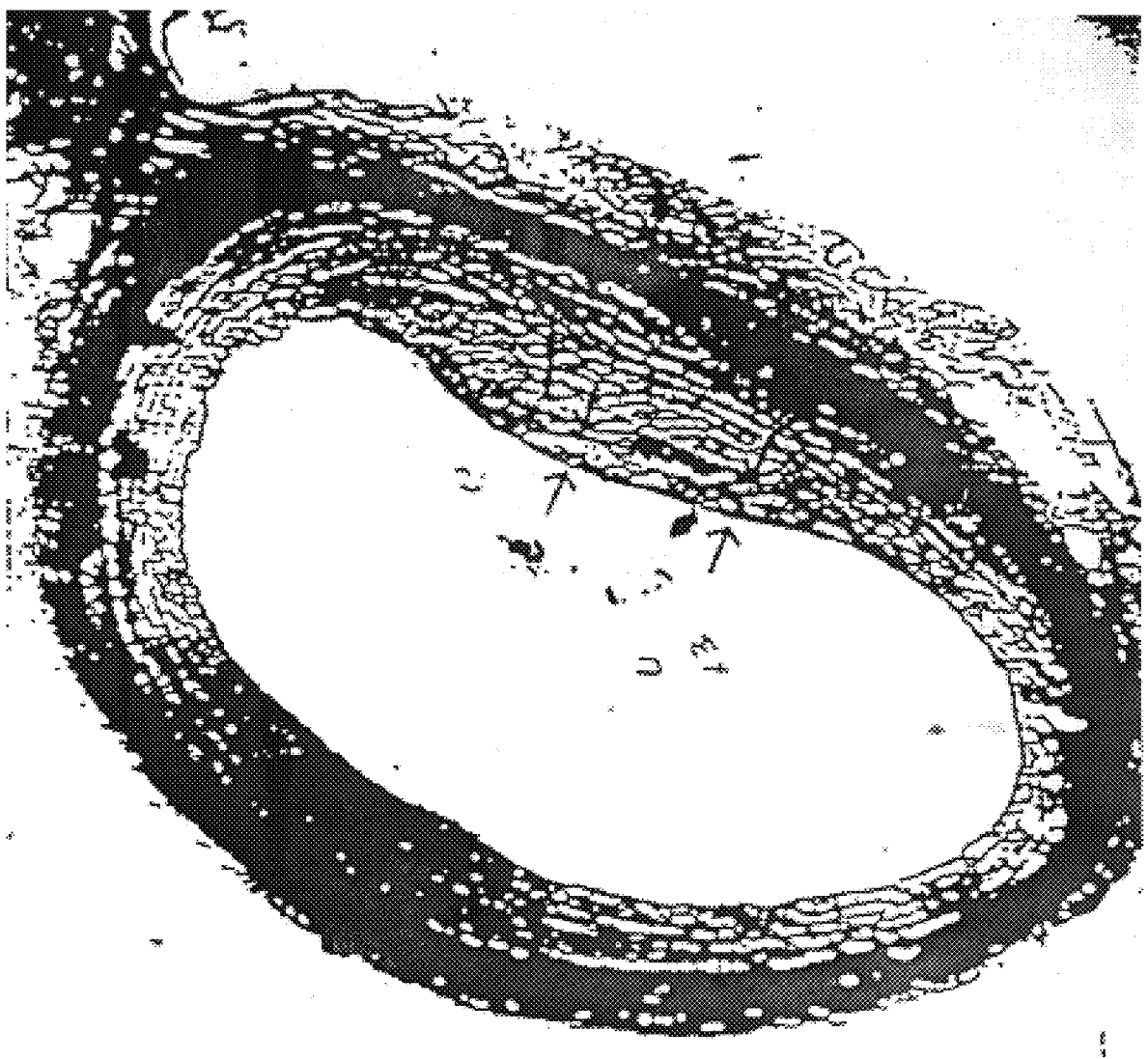
FIG. 2 is a photograph of a cross-section of an exemplary antisense-treated coronary artery.
Figure 3:
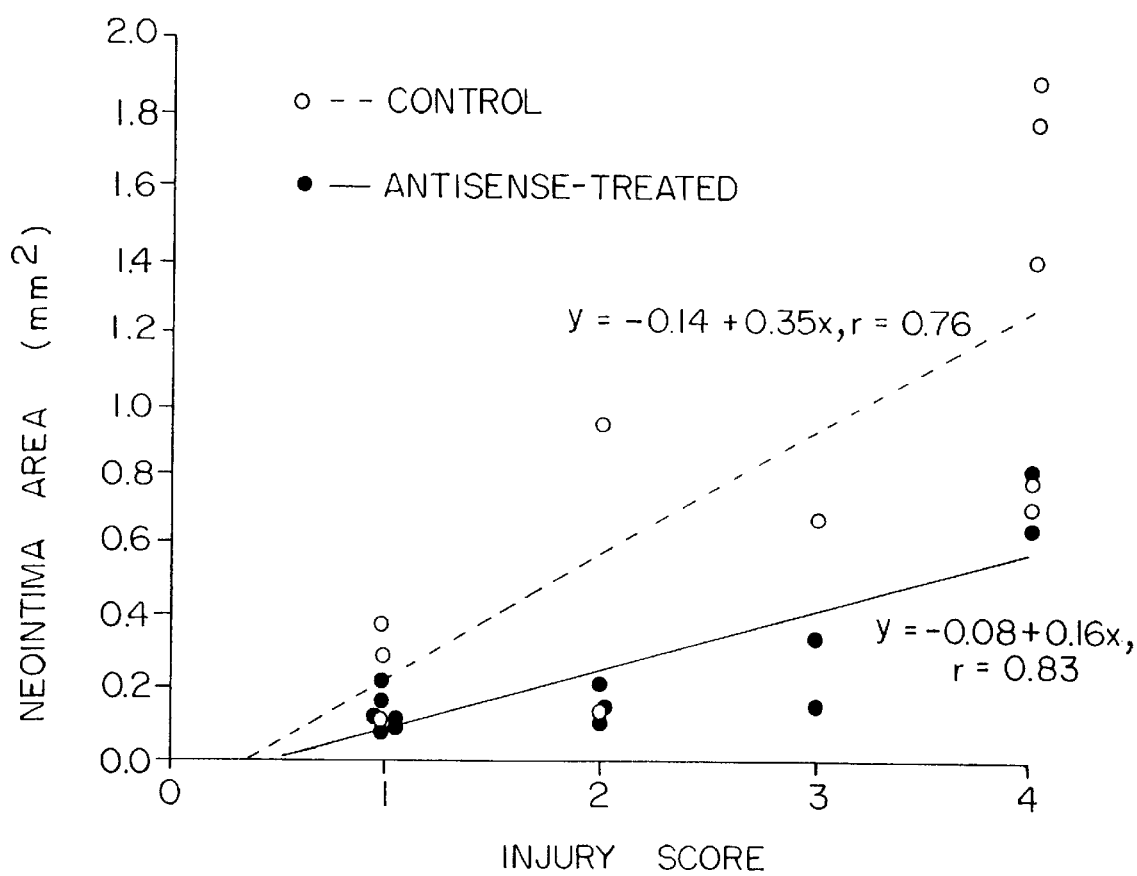
FIG. 3 illustrates maximal neointimal area as a function of degree of injury.

FIG. 1 is a photograph of a cross-section of an exemplary control (i.e., which received sense oligomer injection) coronary artery one month following injury. A significant neointimal thickness is noted (arrows). FIG. 2 is a photograph of a cross-section of an exemplary antisense-treated coronary artery. A marked reduction of the neointima is noted. When maximal neointimal area was analyzed as a function of degree of injury (FIG. 3), regression lines representing the relationship between neointima and injury score (i.e., the severity of injury) showed a significant difference by slopes (p<0.01). As shown in FIG. 3, antisense oligomers significantly reduced neointimal formation, especially with more advanced injury.

Example IV

Inhibition of Extracellular Matrix Production In Human Smooth Muscle Cells By c-myc Antisense Oligonucleotide Treatment This example further demonstrates the effectiveness of c-myc antisense oligonucleotide treatment to inhibit the synthesis of extracellular martrix protein by human smooth muscle cells, in particular procollagen I and III. Antisense treatment greatly reduced extracellular procollagen levels in stimulated human smooth muscle cells (treated with 20% FBS).

A. Measurement of procollagen I and procollagen III by Western blot.

To further determine that c-myc antisense oligonucleotides inhibited the synthesis of extracellular matrix proteins, procollagen I & III was measured from human smooth muscle cells.

Both intracellular and extracellular procollagen (both type I & III) were measured using Western blots. Resting human smooth muscle cells were maintained in medium (Dulbecco's modified eagle's medium) with 0.5% FBS (fetal bovine serum). Human smooth muscle cells were stimulated with or without oligonucleotides in medium containing 20% FBS and ascorbic acid (50 µg/ml). FBS is known to stimulate procollagen synthesis in human smooth muscle cells. At 20 hours after the addition of oligonucleotides cells were washed threes times with phosphate-buffered saline (PBS) and serum-free medium containing 0.1% BSA, ascorbic acid and oligonucleotides was added to the culture for an additional 4 hours. The conditioned medium (medium exposed to cells and oligonucleotides) was collected and proteinase inhibitors including phenylmethylsulfonyl fluoride (PMSF, 0.5 mM), pepstatin (1 µg/ml) and leupeptin (1 µg/ml) were added. The corresponding cell layer was washed three times with cold PBS and lysed in SDS-PAGE sample buffer containing 62.5 mM Tris-HCI, pH 6.8. 20% glycerol, 2% SDS, 5% β-mercaptoethanol for 30 minutes at 4° C. Cell lysates were then boiled for 5 minutes to inactivate proteinases and the supernatants were collected after centrifugation at 10,000 rpm for 10 minutes at 4° C. In selected experiments, cells were continuously incubated with oligonucleotides in 20% FBS-DMEM for 24 hours and samples of culture medium were then subjected to the overnight pepsin digestion (0.1 mg/ml) in 0.5 M acetic acid at 4° C. Individual samples were concentrated 10 fold by centrifugation through a Microcon-30 column (Amicon, Beverly, Mass.) and stored at −20° C. Aliquots were electrophoresed on 65 (w/v) polyacrylamide-SDS gels with 4% stacking regions. The fractionated proteins were then electrotransferred onto PolyScreen PVDF membranes (DuPont NEN, MA) in a transfer buffer containing 192 mM glycine, 25 mM Tris, 0.01% SDS, and 20% methanol. The blots were blocked in 5% non-fat milk and incubated with antibodies against type I collagen (biotin-labeled polycolonal antibody, Southern Biotechnology Associates, Inc. AL) and against type III collagen (Gibco BRL, Gaithersburg, Md.) in 2.5% BSA. The membranes were washed 3 times with PBST (PBS containing 0.1% Tween 20) and incubated with biotinylated secondary antibodies (for type III). The blots were washed and then incubated with streptavidin-peroxidase conjugate (Boehringer Mannheim, Germany) for 30 minutes. After washing, the blots were incubated with Renaissance chemiluminescence reagent (DuPont NEN, MA) for 10 seconds and exposed to Kodak X-Omat film for 30 seconds to 2 minutes. Resulting fluographs were analyzed by laser densitometry (Pharmacia LKB Biotechnology, Inc., Piscataway, N.J.).

c-myc antisense oligonucleotides corresponding to SEQ. ID. NO: 1 were used in all examples, unless otherwise indicated.

Figure 4:
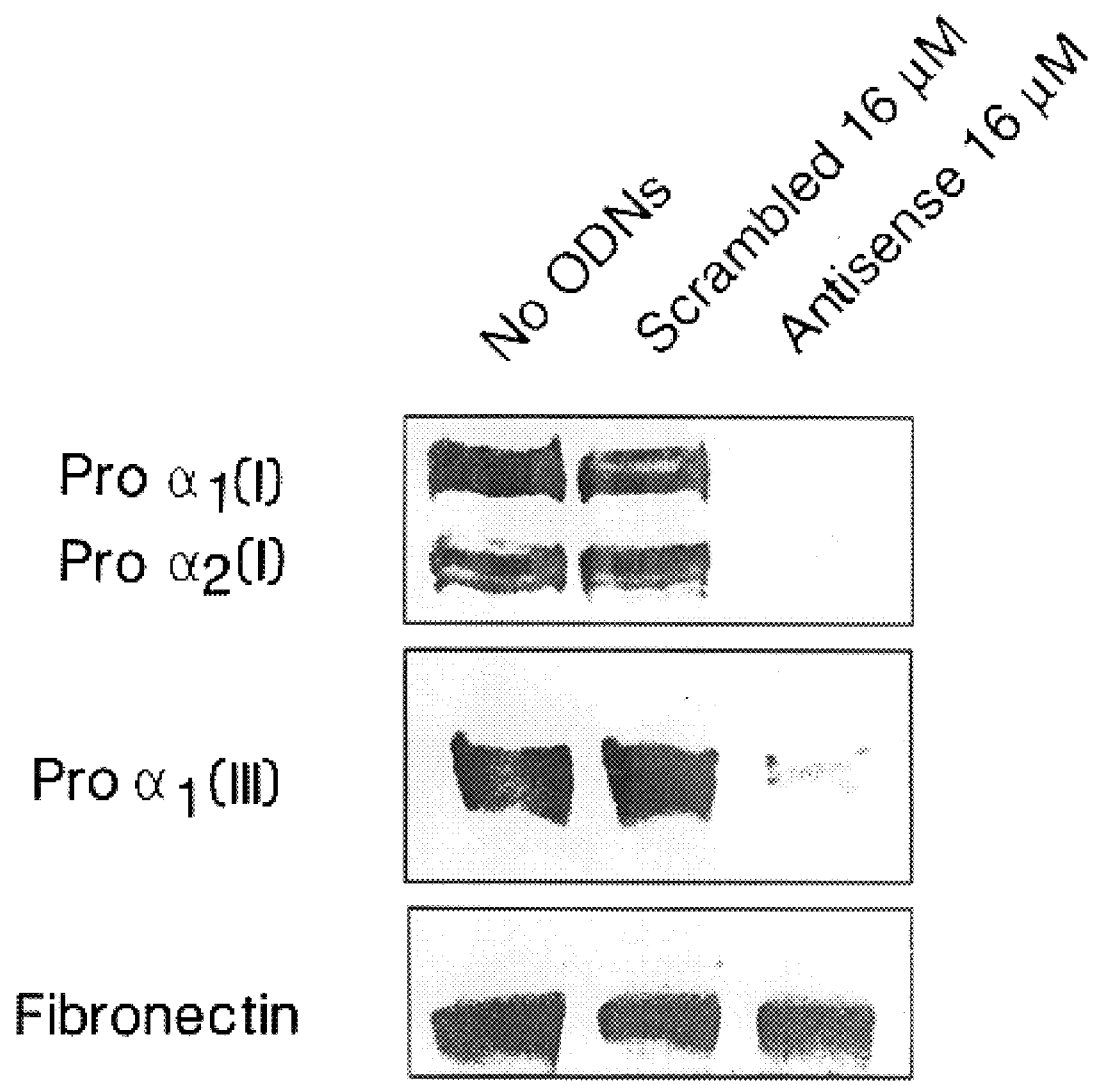
FIG. 4 describes the effect of antisense oligonucleotides targeting the translation initiation region of c-myc mRNA on extracellular levels of procollagen I, procollagen III and fibronectin in post-confluent human smooth muscle cells. Procollagen I and procollagen III in conditioned medium were determined by immunoblotting, whereas fibronectin was measured by immunoprecipitation.

B. Inhibition of the Extracellular Procollagen I and Procollagen III Secretion By c-myc Antisense Oligonucleotides Procollagen levels were determined in post-confluent i.e., density-arrested smooth muscle cells in order to minimize the influence of various growth rates among experimental subgroups. A marked reduction (90%) of extracellular procollagen I and extracellular procollagen III in the conditioned medium was observed following c-myc antisense oligonucleotides treatment as shown by Western blot (FIG. 4). This effect was concentration-dependent in a range of 4–16 µM and it occurred as early as 3 hours following incubation of smooth muscle cells with c-myc antisense oligonucleotides (data not shown).

The reduction in extracellular procollagen I after antisense oligonucleotides was unaffected by the addition of β-aminopropionitrile excluding the possibility that antisense promoted cross-linking of collagen (data not shown).

C. c-myc Antisense Phosphorothioate Oligonucleotides To Exons 1, 2 And 3 Are Effective Inhibitors Of The Synthesis Of Extracellular Matrix Proteins.

Figure 5:
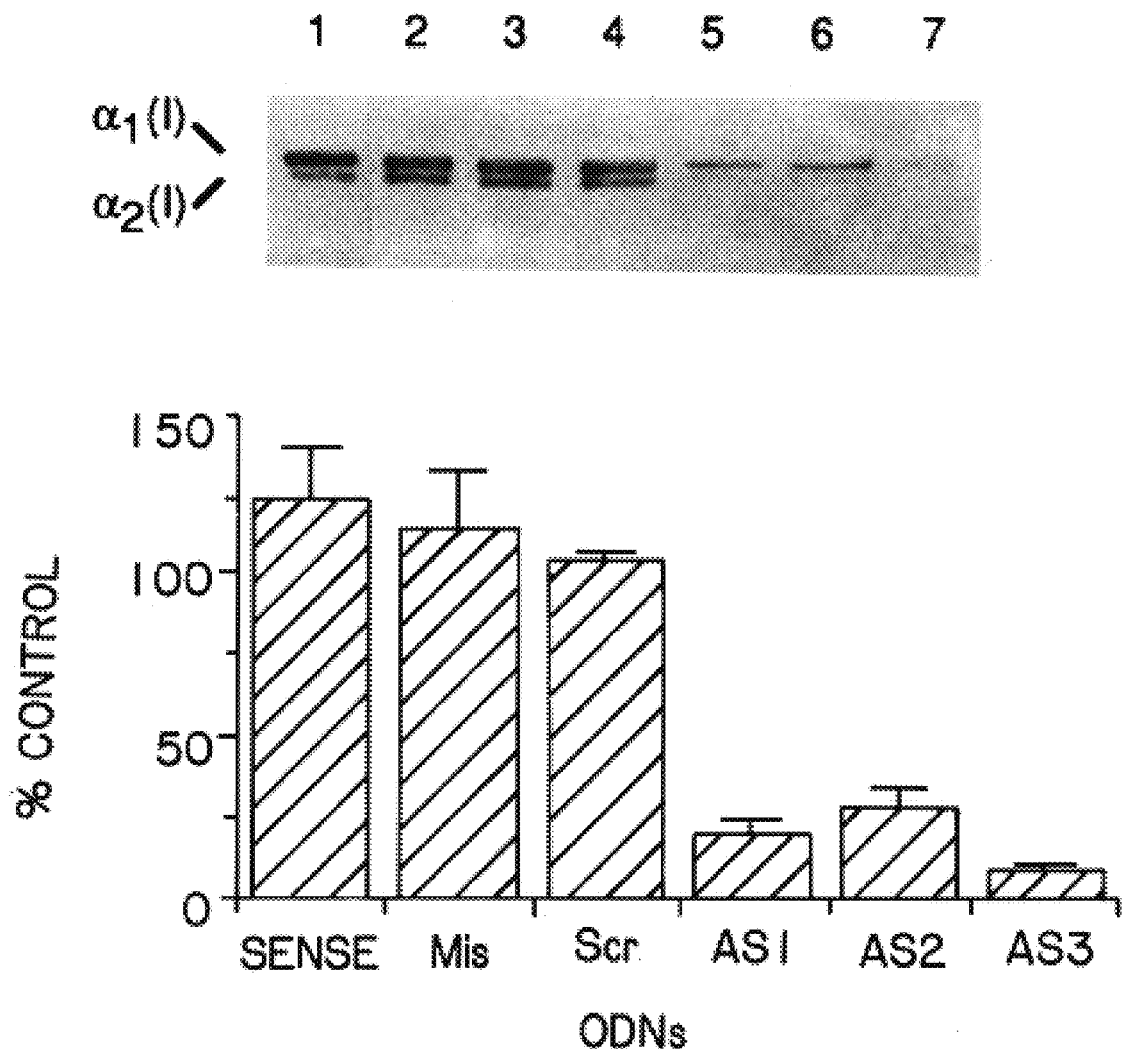
FIG. 5 describes the sequence-specific effect of c-myc antisense oligonucleotides on type I collagen. Smooth muscle cells were incubated with different control oligonucleotides (16 $\mu$M) including sense, 4 bp mismatched and scrambled sequences and antisense oligonucleotides (16 $\mu$M) targeting various regions of c-myc mRNA for 24 hours. The levels of type I collagen in media were measured after conditioned pepsin digestion using Western blot. Top panel.

To further confirm a sequence-specific action of c-myc antisense phosphorothioate oligonucleotides, smooth muscle cells were treated with several control sequences including sense, 4 bp-mismatched and scrambled oligonucleotides (phosphorothioate oligonucleotides are used herein unless otherwise indicated). Their effects on procollagen I levels in the conditioned medium were compared with those after three antisense sequences directed against different regions of c-myc mRNA. As shown in FIG. 5, a consistent reduction in extracellular procollagen I was observed after treatment with different antisense oligonucleotides, whereas control sequences were devoid of such effect.

TABLE III

| SEQ. ID. NO. | OLIGONUCLEOTIDE SEQUENCE (5'→3') | HUMAN c-myc NUCLEOTIDE LOCATION; OLIGONUCLEOTIDE TYPE |
| --- | --- | --- |
| 1 | AACGTTGAGG GGCAT | 559–573; Antisense |
| 2 | ATGCCCCTCA ACGTT | 559–573; Antisense |
| 3 | AACGTGGATT GGCAG | 559–573; Antisense four base mismatch |
| 4 | GAACGGAGAC GGTTT | Scrambled |
| 5 | TATGCTGTGC CGGGGTCTTC GGGC | c-myb; Antisense |
| 6 | GGGAGAGTCG CGTCCTTGCT | 400–419; Antisense |
| 7 | TCATGGAGCA CCAGGGGCTC | 1264–2383; Antisense |

D. Immunoprecipitation of Extracellular Fibronectin and Nuclear c-myc Protein

To determine the effects of oligonucleotides sequences on protein synthesis of extracellular fibronectin and c-myc protein, post-confluent smooth muscle cells were incubated with or without oligonucleotides in methionine-free medium for 4 hours. Afterwards, [$^{35}$]methionine (25 μCl/ml, DuPont NEN, MA) was added for 16 hours and the cell number was counted in a Coulter counter. Extracellular fibronectin in the conditioned medium and c-myc protein in cell nuclear extracts were measured by immunoprecipitation following metabolic labeling.

The conditioned medium was collected after the addition of proteinase inhibitors and aliquots containing equal counters were incubated with antibodies against fibronectin (Becton Dickinson, Bedford, Mass.) for 4 hours followed by Staphylococcus protein A acrylamide beads for an additional 2 hours. After centrifugation, pellets were washed three times, boiled in SDS-PAGE sample buffer for 5 minutes and electrophoresed on a 6% polyacrylamide-SDS gel. The labeled cell layers were washed three times with cold PBS after labeling and lysed in 0.1% NP40, 10 mM Tris (pH 7.9), 10 mM MgCl$_2$, 15 mM NaCl, 5 mM EDTA, 1 mM PMSF, 1 μg/ml leupeptin and 1 μg/ml pepstatin.

In parallel to the extracellular fibronectin assays, cell nuclei were extracted through centrifugation by procedures unknown in the art. The protein concentration in nuclear extracts was measured and aliquots containing 500 μg of protein were incubated with anti-c-myc antibody, pan-myc, (gift from G. I. Evan), for 12 hours and then with Staphylococcus protein A acrylamide beads for an additional 90 minutes. After washing, the beads were collected and boiled in SDS-PAGE sample buffer and the soluble fraction was electrophoresed on SDS-PAGE. The gel was dried and exposed to Kodak-Omat film at −70° C. for 5–7 days.

E. Levels of Extracellular Fibronectin Were Unchanged By c-myc Antisense Oligonucleotides, While c-myc Protein Levels Decreased In contrast to a significant reduction in extracellular procollagens, the levels of extracellular fibronectin in the conditioned medium were not significantly affected (FIG. 4) pointing to selective effects of antisense oligonucleotides. The incubation of post-confluent smooth muscle cells with c-myc antisense oligonucleotides (16 μM) resulted in down-regulation of c-myc protein in nuclear extracts (FIG. 6).

Example V c-myc Antisense Oligonucleotides Do Not Alter Human Smooth Muscle Cell Overall Metabolism To further ensure that oligonucleotides did not produce other changes in smooth muscle cell function, assays of cell membrane integrity, cell metabolism and induction of genes related to collagen synthesis or degradation pathways were conducted.

Human smooth muscle cells were assayed for cell membrane integrity using trypan blue. More than 95% of cells remained viable following treatment with various oligonucleotides (16 μM) as assessed by trypan blue exclusion.

To determine total protein synthesis aliquots of the conditioned media were precipitated in cold 10% trichloroacetic acid (TCA) for 30 minutes at 4° C. and pellets were washed twice in 5% TCA. The pellets were then dissolved in Solvable (DuPont NEN, MA) and the incorporated radioactivity was measured in a scintillation counter (Pharmacia LKB Biotechnology Inc. Piscataway, N.J.). The overall protein synthesis, as measured by [$^{35}$S]methionine incorporation as discussed herein, was comparable in smooth muscle cells incubated with or without antisense (SEQ. ID. NO: 1) oligonucleotides (FIG. 7). Note that cells stimulated with 20% FBS showed increased protein synthesis compared to unstimulated cells treated with only 0.5% FBS. c-myc antisense oligonucleotide treatment did not reduce protein synthesis compared to sense, mismatch and no oligonucleotide controls.

In addition, the level of procollagen I in the conditioned medium was restored to control levels 24 hours after the removal of c-myc antisense oligonucleotides (FIG. 8). These results indicated that antisense (SEQ. ID. NO: 1) oligonucleotides produced a selective but reversible reduction of extracellular procollagens preserving normal metabolic activity of vascular smooth muscle cells.

Because antisense oligonucleotides may induce expression of non-targeted genes, the collagenolytic activity and interferon-γ levels following treatment with c-myc antisense oligonucleotides was determined to exclude these non-specific effects.

Post-confluent smooth muscle cells were incubated with serum-free medium with or without oligonucleotides. The aliquots of medium were collected 24 hours thereafter. Matrix metalloproteinase activities were determined after selective destruction of tissue inhibitor of metalloproteinase by dithiothritol and iodoacetamide. Latent collagenases produced by human smooth muscle cells were activated with aminophenylmercuric acetate, and then incubated with type 1 collagen or gelatin and cleavage products assessed by SDS-PAGE (the methods of D. D. Dean, et al., J. Clin. Invest., 84:678–685 (1989) and P. E. Desrochers, et al., J. Biol. Chem 267:5005–5012 (1992) are incorporated by reference herein). Metalloproteinases were characterized by SDS-substrate gel electrophoresis (i.e., zymography) under nondenaturing conditions using either β-casein or gelatin as substrates. Comparable collagenolytic activity against type I collagen and gelatin were exhibited in conditioned medium from control, sense- and antisense- (SEQ. ID. NO: 1) treated smooth muscle cells (data not shown), suggesting that c-myc antisense oligonucleotides did not increase endogenous collagenolytic activity.

To determine whether c-myc interferon-γ, a potent inhibitor of type I collagen synthesis, was inadvertently induced, interferon-γ was assayed in the culture medium and human smooth muscle cells. Interferon-γ was undetectable in the conditioned culture media and cell lysates after incubation with c-myc antisense (SEQ. ID. NO:1) oligonucleotides using ELISA method.

Example VI

No Effect Of c-myc Antisense Oligonucleotides On Procollagen α$_1$(I), α$_2$(I) and α$_1$(III) mRNAs In Human Smooth Muscle Cells This example demonstrates that c-myc antisense oligonucleotide treatment does not decrease the mRNA of procollagens in human smooth muscle cells.

To measure mRNA from procollagen post-confluent smooth muscle cells were incubated with or without oligonucleotides for 24 hours, washed three times with cold PBS and lysed in 4 M guanidinium isothiocyanate. Total RNA was isolated by phenol-chloroform extraction followed by isopropanol precipitation. The total RNA was quantitated by spectrophotometric absorbance at 260 nm. Equal amounts of RNA samples (10 μg) were denatured and separated on 0.8% agarose/formaldehyde gels and blotted onto nitrocellulose membranes. The RNA was crosslinked to nitrocellulose membranes using a UV crosslinker (Stratagene, Calif.). The blots were hybridized at 42° C. for 24 hours with human procollagen $\alpha_1$(I) (ATCC) and human procollagen $\alpha_2$(I) (gift from H. Kuivaniemi) cDNA probes. The probe for 7S ribosomal RNA were used as control The probes were labeled with $^{32}$P-CTP by nick translation to a specific activity of greater than $10^8$ cpm/μg DNA. The blots were sequentially washed twice in 2x, 1x, 0.5x and 0.1x SSC-0.1% SDS at 42° C. for 15 min. Each wash was repeated twice. Blots were exposed to Kodak-Omat film at −70° C. with an intensifying screen for 6 hours to 3 days.

Downregulation of c-myc protein after antisense treatment raises the possibility of transcriptional regulation of collagen expression. Accordingly, procollagen $\alpha_1$(I) and procollagen $\alpha_2$(I) mRNA levels were analyzed in smooth muscle cells after their incubation with or without oligonucleotides using Northern blot analysis. As shown in FIG. 9, antisense oligonucleotides did not affect procollagen $\alpha_1$(I) and procollagen $\alpha_2$(I) mRNA levels. Likewise, similar levels of procollagen $\alpha 1$(III) mRNA were seen with or without c-myc antisense oligonucleotides (data not shown). 7S RNA remained unchanged in all three experimental conditions.

Example VII

Intracellular Accumulation Of Procollagen In Human Smooth Muscle Cells Treated With c-myc Antisense Oligonucleotides This example demonstrates that c-myc antisense oligonucleotide treatment increases procollagen inside human smooth muscle cells. These results are consistent with the decrease in extracellular matrix procollagen synthesis in the presence of c-myc antisense oligonucleotides.

A. Intracellular Procollagen Levels Are Increased by c-myc Antisense Treatment.

To examine mechanisms involved in the reduction of extracellular procollagen by c-myc antisense oligonucleotides, the secreted and intracellular procollagens were determined following 4 hours of [$^{14}$C]proline labeling.

To measure intracellular procollagen after c-myc antisense oligonucleotide treatments, cells were incubated with or without oligonucleotides for 20 hours in 20% FBS-DMEM. Serum-free medium containing ascorbic acid (50 μg/ml), [$^{14}$C]proline (2.5 μCI/ml, DuPont NEN, MA) and oligonucleotides were added to the cells for the additional 4 hours. The culture medium was collected and proteinase inhibitors were added. Aliquots of media were centrifuged through Microcon-30 column in order to remove unincorporated radioisotope and to concentrate samples for electrophoresis. The corresponding cell layers were then washed 3 times with cold PBS, lysed in PAGE-SDS sample buffer and boiled for 5 minutes to inactivate proteinases. The aliquots of concentrated medium, cell lysates (from equal cell number) and procollagen I purified from human skin fibroblast cells (gift from W. Arnold) were electrophoresed on 6% polyacrylamide-SDS gels with 3% stacking regions. The gels were fixed for 30 minutes in 10% acetic acid, 20% methanol, dried and exposed to film at -70° C. for 7 days.

c-myc antisense treatment decreased in secreted [$^{14}$C] proline labeled procollagen and was similar to the Western blot DNA. c-myc antisense treatment significantly increased the intracellular concentration of procollagen I compared to untreated cells and cells treated with a scrambled oligonucleotide (FIG. 10).

B. The Increase In Intracellular Procollagen Level Is Not Due To The Inability Of Human Smooth Muscle Cells To Hydroxylate Proline After c-myc Antisense Oligonucleotide Treatment.

The intracellular accumulation of procollagen may reflect the inhibition of post-translational modifications required for the assembly of procollaaen α chains into a triple-helical conformation. Therefore, to rule out this possibility, the affects c-myc antisense treatment of prolyl 4-hydroxylase activity and hydroxyproline content were measured.

Post-confluent smooth muscle cells were incubated with or without oligonucleotides in 20% FBS-DMEM for 24 hours as described above. Cell layers were washed with cold PBS 3 times and lysed in 0.2 M NaCI, 20 mM Tris-HCI, pH 7.4, 0.1% Triton x-100, 0.1 M glycine and 10 μM DTT (the methods of K. J. Kivirikko, et al., Methods in Enzymology, 82:245–364 (1982) are incorporated by reference herein). The lysates were then sonicated for 30 seconds on ice and protein concentration was measured. The remaining cell lysates were centrifuged at 13,000 rpm for 20 minutes at 4° C.

The aliquots of supernatant were assayed for prolyl 4-hydroxylase activity by measuring the formation of radioactive 4-hydroxyproline using a [$^{14}$C] proline-labeled procollagen I as substrate (the methods of K. J. Kivirikko, et al., Anal. Biochem., 19:249–255 (1967) are incorporated by reference herein). The aliquots of cell lysate were hydrolyzed, hydroxyproline was assayed by a specific chemical procedure.

Prolyl 4-hydroxylase activity, a pivotal enzyme controlling triple helix formation, was similar among experimental subgroups. It was 11.7±0.1 (dpm/μg protein, mean±SD of 2 separate experiments) in control smooth muscle cells treated with no oligonucleotides, 12.±2.3 in cells incubated with scrambled oligonucleotides (16 μM) and 10.5±2.0 after treatment with c-myc antisense oligonucleotides (16 μM).

Hydroxyproline content was greater in c-myc antisense (SEQ ID NO:1) cells than in untreated or scrambled oligonucleotide treated cells (FIG. 11). The increase in hydroxyproline content reflects the increase in procollagen levels, which is a substrate for prolyl 4-hydroxylase.

Example VIII

Inhibition of Extracellular Matrix Production in Human Fibroblasts Human Skin Fibroblasts Cells Using c-myc Antisense Oligonucleotides This example further demonstrates the effectiveness of c-myc antisense oligonucleotide treatment to inhibit the synthesis of extracellular martrix protein by human skin fibroblast cell, in particular procollagen I and III. Antisense treatment greatly reduced extracellular procollagen levels in stimulated human skin fibroblast cells (treated with 20% FBS).

A. Assay of Extracellular and Intracellular collagen I and III Using Western Blots To further determine whether c-myc antisense oligonucleotides inhibited the synthesis of extracellular and intracellular procollagen I and III in human skin fibroblasts, procollagen levels were determined, as discussed for human smooth muscle cells in Example IV and VII. Human skin fibroblasts cells used in the human skin fibroblast experiments were confluent. Cells were obtained and cultured as in Example II and by methods known in the art.

B. Rapid Inhibition of Extracellular Collagen I and III Secretion By c-myc Antisense Oligonucleotide Treatment These experiments show that c-myc antisense oligonucleotides inhibit the secretion of extracellular collagen I and III by human skin fibroblasts in a dose-dependent, antisense sequence dependent manner and with a rapid time course of inhibition.

To further determine the dose response and antisense specificity of c-myc antisense oligonucleotides for inhibition of extracellular matrix production, extracellular collagen I was measured using Western blots of human fibroblast cell protein isolated from human fibroblasts subjected to different treatments. Human fibroblast cells were exposed to either scrambled oligonucleotides (SEQ ID NO:4; 16 μM), mismatched oligonucleotides (SEQ ID NO:3; 16 μM), antisense oligonucleotides (SEQ ID NO: 1; 4, 8 and 16 μM) or no oligonucleotides for 24 hours as discussed herein and the proteins of those cells were assayed for collagen I in the Western blot shown in FIG. 12, lanes 1–5, respectively. The double band reflects collagen $\alpha_1(I)$ and $\alpha_2(I)$ chains, upper and lower bands, respectively. Antisense treated cells showed a proportional decrease of the amount of collagen I with increasing levels of c-myc antisense oligonucleotide, while the control treatments (no treatment scrambled and mismatch) showed higher amounts of collagen than the lowest concentration of c-myc antisense oligonucleotide used. These results taken together with the other results discussed herein, especially the lack of up regulation of collagen and procollagen degradation pathways by c-myc antisense treatment, show that extracellular matrix production, in particular procollagen I secretion is inhibited by c-myc antisense treatments.

The time course of c-myc antisense oligonucleotide treatment of human skin fibroblast cell collagen I secretion showed rapid inhibition of secretion of de novo synthesized collagen I. At time zero human skin fibroblast cells were exposed to fresh medium (as used herein "fresh medium" is medium containing 20% FBS and ascorbic acid 50 μg/ml and other components as indicated) with either no oligonucleotides, scrambled oligonucleotides, or antisense oligonucleotides for 24 hours (concentration of the oligonucleotides was 16 μM; SEQ ID NOS: 1 and 3). At three, six and twenty four hours aliquots of each cell medium were taken and assayed for the presence of collagen I by Western blot, as discussed herein. A reduction in collagen I level was observed in the antisense treated cells compared to the control cells (untreated and scrambled treated) in as early as three hours. At twenty four hours the antisense treated cells showed at least 5 to 10 times less secreted collagen I than the control cells. The six hour value produced intermediate results.

The secretion of collagen III by human fibroblast cells was also inhibited by c-myc antisense oligonucleotides. Human fibroblast cells were treated with fresh medium containing either no oligonucleotides, 16 μM scrambled oligonucleotides or 16 μM c-myc antisense oligonucleotides for twenty four hours and the medium was assayed for the presence of extracellular collagen III at the end of the twenty four hours. No extracellular collagen III was observed in the antisense treated cells, while the control cells (no treatment and scrambled treated) showed the presence of extracellular collagen III (at least 10–100 times higher level of collagen III, as compared to the antisense treat cells).

Thus, these results taken together with the other results discussed herein, show that extracellular matrix production, in particular procollagen I and III secretion, is inhibited by c-myc antisense treatments.

C. Accumulation Of Intracellular Procollagen I And Simultaneous Decrease In Extracellular Procollagen I By c-myc Antisense Oligonucleotide Treatment Inhibition of procollagen secretion by c-myc antisense treatment of human fibroblast cells was associated with an accumulation of intracellular procollagen I. Human fibroblast cells were treated with fresh medium containing either no oligonucleotides, 16 μM scrambled oligonucleotides, or 16 μM c-myc antisense oligonucleotides for twenty four hours and the medium and the corresponding human fibroblast cells were assayed for the presence of extracellular procollagen I and intracellular procollagen I using $^{14}C$ proline labelled protein synthesis products separated as discussed herein. In FIG. 13, the major bands in lanes 1-3 show procollagen $\alpha_1(I, III)$ and $\alpha_2(I)$ chains. The amount of secreted procollagen I is reduced at least 10–20 times in the antisense treated cells compared to the control cells (no treatment, scrambled treated, lanes 1 and 2, respectively). The upper band in lanes 1–3 is approximately 116 Kd ("upper band"), which corresponds to procollagen $\alpha_1(I, III)$; the lower band in lanes 1–3 (from left to right) is approximately 100 Kd, which corresponds to $\alpha_2(1)$. In FIG. 13, lanes 4–6 show intracellular procollagen I is at least five times greater in antisense treated cells (lane 6) than the control cells (lanes 4 and 5). In FIG. 13, lane 7 shows the molecular weight markers.

Thus, these results demonstrate that c-myc antisense treatment decreases the amount of procollagen secreted by human fibroblast cells and increases the amount of procollagen in the cells.

Example IX c-myc Antisense Oligonucleotides Did Not Change The Thermal Stability Of Intracellular Procollagen In Human Skin Fibroblasts The tertiary structure of intracellular procollagen was not changed by c-myc antisense treatment. Human fibroblast cells were treated with fresh medium containing either no oligonucleotides, 16 μM scrambled oligonucleotides, or 16 μM c-myc antisense oligonucleotides for twenty four hours. The melting temperature of procollagen from each experimental condition was measured as discussed herein and known in the art. FIG. 14 shows that the melting profile for control cells (untreated and scrambled treated) and antisense treated are similar. These results demonstrate that the procollagen present inside of antisense treated cells maintains a normal triple-helical conformation that is the same as in control treated cells.

Thus, c-myc antisense treatment does not lead to a detectable alteration of procollagen structure that could lead to increased intracellular degradation or decreased protein export from the cell.

Example X c-myc Antisense Oligonucleotide Treatment Did Not Change The Procollagen $\alpha_1(I)$ mRNA Level In Human Skin Fibroblasts This example demonstrates that c-myc antisense oligonucleotide treatment does not inhibit the synthesis of extracellular martrix protein by human skin fibroblast cells, in particular procollagen I, by reducing the mRNA level of procollagen. Antisense treatment did not reduce mRNA procollagen levels in stimulated human skin fibroblast cells (treated with 20% FBS).

A. Measurement of Procollagen $\alpha_1(I)$ mRNA

RNA was isolated and Northern analysis was carried out as follows: Cells were washed three times with cold PBS buffer and lysed in 4 M guanidinium isothiocyanate. RNA was extracted by phenol/chloroform and quantitated by spectrophotometric absorbance at 260/280 nm. RNA samples (20 μg) were separated by electrophoresis on 0.8% agarose-formaldehyde gels. Following transfer of the RNA to nitrocellulose filters, blots were fixed by ultraviolet irradiation. The blots were prehybridized in 5× standard saline citrate, 2× Denhardt's solution, 0.1% SDS and 0.2mg/ml of denatured salmon sperm DNA for at least 4 hours at 65° C. Hybridization was performed overnight using the same buffer containing cDNAs radio labeled with $^{32}$p dCTP by nick translation to a specific activity of approximately 108–109 cpm/μg. Blots were washed at 65° C. in 0.5× standard saline citrate and 0.1% SDS. The filters were exposed to Kodak X-Omat film at −70° C. with intensifying screens for 1–5 days. The autoradiography of the resulting Northern blots was quantitated by scanning densitometry and integration of peak areas. The probes used for this study were as follows: a 1.8 Kb pro-alpha 1(1) (HF-677) cDNA corresponding to the COOH-terrninal propeptide and the carboxy-terminal portion of the triple helical region of human pro-alpha 1(1) chain of type I procollagen (Chu et al., Nucleic Acids Res. 10:5925–5934, 1982).

B. Procollagen $\alpha_1(I)$ mRNA Levels Are Not Decreased By c-myc Antisense Treatment The mRNA level of procollagen alpha I in human fibroblast cells was unaffected by c-myc antisense treatment. Human fibroblast cells were treated with fresh medium containing either no oligonucleotides, 16 μM scrambled oligonucleotides, or 16 μM c-myc antisense oligonucleotides for twenty four hours. mRNA was purified from each experimental condition and analyzed for the presence of procollagen alpha I mRNA, as discussed herein and known in the art. FIG. 15 shows that control cell procollagen I mRNA (untreated and scrambled treated; lanes 1 and 2, respectively) levels are similar to the antisense treated cell procollagen alpha I mRNA levels (lane 3). These results demonstrate that c-myc antisense treatment of human fibroblast cells does not down regulate mRNA transcription of the procollagen alpha I gene.

Thus, taken together with the other results discussed herein, the mRNA results show that c-myc antisense treatment decreases the secretion of procollagen I and III, which are proteins that lead to the synthesis of collagen in the extracellular matrix.

Example XI c-myc Antisense Oligonucleotides Did Not Alter The Recovery Of The Synthesis Of Extracellular Matrix Protein After the Cessation Of c-myc Antisense Oligonucleotide Treatment of Human Skin Fibroblasts The ability of human fibroblast cells to synthesize collagen I after removal of c-myc antisense oligonucleotide treatment was not impaired. Human fibroblast cells were treated with fresh medium containing either no oligonucleotides, 16 μM scrambled oligonucleotides, or 16 μM c-myc antisense oligonucleotides for twenty four hours. Human fibroblast cells from each experimental condition were then exposed to fresh medium without any oligonucleotide additions and assayed for the presence of extracellular collagen I, as discussed herein. FIG. 16 shows that control cells (untreated and scrambled pretreated) and antisense treated cells produced similar levels of extracellular collagen I twenty four hours after abatement of the treatment. These results demonstrate that after twenty four hours there was full recovery of collagen production in c-myc antisense treated human fibroblast cells.

Thus, c-myc antisense treatment did not produce any cytotoxic effects that resulted in the inability of the cell to return to pretreatment secretion levels of procollagen.

Example XII

Inhibition of Synthesis of Extracellular Matrix In Pig Coronary Arteries

This example further demonstrates the in vivo effectiveness of localized c-myc antisense oligonucleotide treatment to decrease the progression of extracellular matrix synthesis after tissue trauma. This example also further demonstrates the in vivo effectiveness of c-myc antisense treatment in decreasing the progression of internal organ scaring, as well as decreasing the progression of tissue scaring associated with the synthesis of extracellular matrix molecules, such as collagen.

A. Inhibition of The Production of Extracellular Matrix Fibrillar Material By c-myc Antisense Oligonucleotide Treatment To determine the effects of c-myc antisense treatment on the progression of extracellular matrix synthesis after tissue trauma, pig hearts were injured in vivo, treated with oligonucleotides as discussed in Example III (unless otherwise indicated), and sacrificed at three days, seven days, and twenty eight days after the delivery of oligonucleotides. The same c-myc antisense and sense oligonucleotides (SEQ ID NO: 1 and 2) and dosages (1 mg per artery) were used as in Example III.

Cross-sections of traumatized (injured) coronaries from antisense treated pigs showed differences in microscopic extracellular architecture compared to the sense treated traumatized coronaries. Traumatized coronaries from each experimental group were examined as blind samples with light microscopy, magnification 20–62×. Tissue was stained with Verhoff-Van-Gieson stain, as known in the art, to highlight cells and extracellular matrix, and sirus red stain, as known in the art, to highlight collagen. The c-myc antisense treated vessels, which displayed a smaller neointima area compared to control vessels, also displayed less red staining than the control vessels (sense treated). The antisense treated coronaries showed less extracellular fibrillar material compared to the sense treated coronaries; and the antisense treated coronaries showed less extracellular space between cells. Neointimal smooth muscle cell proliferation was also assessed using immunostaining for PCNA (Proliferating Cell Nuclear Antigen) following balloon denudation and transcatheter delivery of c-myc sense (S) or antisense (AS) oligonucleotides (1 mg) into porcine coronary arteries, see Table IV. Antisense treatment of coronaries inihibited the progression of smooth muscle cell proliferation caused by tissue trauma compared to sense treatment of coronaries. PCNA staining permitted the assessment of the number of proliferating cells in a given neointima cross-section. Generally 200–1,000 cells were counted and the percentage of proliferating smooth muscle cells determined and expressed as the proliferative index. The proliferative index (PI), neointirna/media (I/M) ratio and the reduction in I/M ratio (ΔI/M) were as follows:

TABLE IV

| Day | $R_x$ | n | P* (%) | I/M ratio | ΔI/M (%) |
|---|---|---|---|---|---|
| 3 | S | 4 | 5 ± 2 | 0.09 ± 0.03 | |
| | AS | 8 | 3 ± 5 | 0.05 ± 0.02 | ↓44 |
| 7 | S | 4 | 47 + 13 | 0.28 ± 0.04 | |
| | AS | 8 | 11 ± 13** | 0.12 ± 0.05** | ↓57 |
| 28 | S | 6 | N/A | 1.19 ± 0.51 | |
| | AS | 4 | N/A | 0.47 ± 0.30* | ↓61 |

P* - proliferating cells/total number of cells × 100, *p(0.05, **p(0.01

Coronaries with a reduction of the I/M ratio have an improved lumenal diameter. These results demonstrate that localized c-myc antisense treatment inhibits smooth muscle cell growth and extracellular matrix formation over time.

Thus, localized c-myc antisense treatment inhibits the progression of scar formation in a traumatized tissue, such as scar formation in coronaries after balloon angioplasty trauma caused by smooth muscle cell proliferation and extracellular matrix formation.

Example XIII

Rapid Localization c-myc Antisense Oligonucleotides In Pig Coronary Arteries This example demonstrates the in vivo effectiveness of c-myc antisense oligonucleotides in penetrating vascular and connective tissues using local delivery devices. In conjunction with the other results discussed herein, these results demonstrate the ability of c-myc antisense treatment to localize in cell nuclei within 30 minutes and before the onset of c-myc induction (which occurs over three to four hours). The local distribution of c-myc antisense oligonucleotides after local administration to the vessel wall of coronary arteries decreases scar formation following balloon angioplasty.

A. Local Delivery Of c-myc Antisense Oligonucleotides Labelled With Either Carboxyfluorscein Or $^{35}$S Phosphothioate The c-myc antisense oligonucleotides used in this Example were prepared as discussed herein. Phosphorothioate antisense oligonucleotides (SEQ. ID NO:1) directed against the translation initiation region of the human c-myc gene used in the distribution studies labeled with carboxyfluorosceins (480 nm excitation, 520 nm emission, Molecular Probes, Inc.) as previously described in Iverson, et al, Antisense Res. Dev. 2: 211–222 (1992), the methods of which are herein incorporated by reference. For the quantitative studies oligonucleotides were $^{35}$S-labeled at each internucleotide link with the specific activity of $1.8 \times 10^8$ cpm/$\mu$mol.

Domestic crossbred pigs (Sus scrofa) were used and prepared for experiments as discussed herein. A coronary ostia was canulated using a 9 French SAL 1 guiding catheter (Cordis Corp., Miami, Fla.) was under fluoroscopic guidance. After intracoronary injection of nitroglycerin (100 $\mu$g), a baseline coronary angiography was obtained. Selected portions of the coronary arteries were then subjected to denudation (traumatization) with an oversized balloon inflated 3 times (6 atm) for 30 sec. Then, the delivery device, a Kaplan-Simpson Infusasleeve (of LocalMed, Palo Alto, Calif.) was advanced over a standard angioplasty balloon ("support" balloon) to the region of interest. This device consists of multilumen infusion region (18 mm) containing multiple sideholes (40 $\mu$m) which are juxtapositioned against the vessel wall by inflating a support balloon. The device used in studies infuses solutions using rigid, noncollapsable channels. This design minimizes drug loss to the bloodstream and permits separate control of drug infusion and placement of the drug delivery device in the vessel. After a full expansion of the internal balloon catheter, the infusion portion was fluoroscopically ascertained, c-myc antisense oligonucleotides were administered. Intramural injections were carried out under 100 PSI of the external pressure. The total volume of the injectate was 5–6 ml, delivered by the external pump at 40 ml/min. The administered dose was 1 mg per artery. After injection was completed, devices were removed and final angiograms were recorded. To verify proper conditions of oligonucleotides delivery, serial quantitative coronary angiography was employed to measure the initial luminal diameter of selected coronary arteries, luminal diameter prior to oligonucleotides delivery (i.e., after denuding injury) and after oligonucleotides administration. In addition, diameters of denudation and support balloons were measured in situ. Guiding catheter was used as a scaling device for all angiographic measurements. At the indicated times, the animals were given a lethal dose of sodium pentobarbital (100 mg/kg iv).

As shown in Table V, mean luminal vessel diameter was 2.5±0.1 mm at baseline. The coronary arterial injury was produced with the oversized balloon (also known as denuding) (mean balloon:artery ratio 1.1). All vessels remained patent following balloon overstretch with mean luminal diameter of 2.6±0.1 mm. C-myc antisense oligonucleotides were administered through expanded delivery device achieving direct contact with the endoluminal surface or the vessel (mean balloon:artery ratio 1.0).

TABLE V

Angiographic Characteristics Based On Quantitative Coronary Angiography (n = 14).

| | |
|---|---|
| Initial luminal diameter (mm) | 2.5 ± 0.1 |
| Denuding balloon/artery ratio | 1.1 ± 0.0 |
| Post-denudation luminal diameter (mm) | 2.6 ± 0.1 |
| Delivery balloon/artery ratio | 1.0 ± 0.0 |
| Post-delivery luminal diameter (mm) | 2.6 ± 0.1 |

B. Qualitative Assessment of oligonucleotides Delivery

To determine distribution of fluorescent-labeled oligonucleotides after transcatheter delivery, the coronary arteries were excised with adjacent tissues. After the vessel lumen was flushed with PBS, the arteries were fixed in 10% buffered formalin for 6 hours and embedded in paraffin. The arteries were cut into serial 4-$\mu$m-thick sections (50 mm per vessel including 18 mm injected portion. The examination of the site of injection as well as proximal and distal portions of the vessel provided information regarding the longitudinal oligonucleotides distribution. In addition, noninjected coronary artery from the same animal served as the additional control. The sections were deparaffmized end covered with SlowFade-Light antifade reagent (Molecular Probes, Inc., Eugene, Oreg.). Each slide contained the vessel, periadventitial tissue and adjacent myocardium (FIG. 17) which allowed to determine the depth of oligonucleotide penetration. The fluorescent-labeled antisense oligonucleotides were visualized under Nikon Optiphot microscope equipped for epifluorescence with XF-22 filter. Photographs were taken on Kodak Ektachrome P1600 films.

To analyze intracellular localization of fluorescent labeled oligonucleotides in vitro and in vivo, laser scanning confocal microscope (model Zeiss Axiovert 100) adapted with MRC-600 krypton-argon laser (Bio-Rad) was used. The krypton-argon laser emits laser lines at excitation wavelength 488 nm. The induced fluorescent light is scanned through a 63× objective and converted to a video signal for display on a computer screen. The images were photographed off the computer screen on Kodak Ektachrome 100 films. For in vitro studies, in order to determine the time course of oligonucleotides uptake by vascular smooth muscle cells, cells were grown on chamber slides in medium containing 10% fetal bovine serum for 2 days and fluorescein-labeled oligonucleotides were added (8 $\mu$M) for 2, 30 minutes and 2 hours. Then, cells were washed 3 times with PBS and fixed in 50% acetone and 50% methanol. For in vivo studies, sections of the coronary arteries obtained as described above were analyzed by confocal microscopy at 0.4–0.5 $\mu$m optical thickness.

C. Distribution Of Antisense Oligonucleotides In The Vessel Wall

Figure 18A:
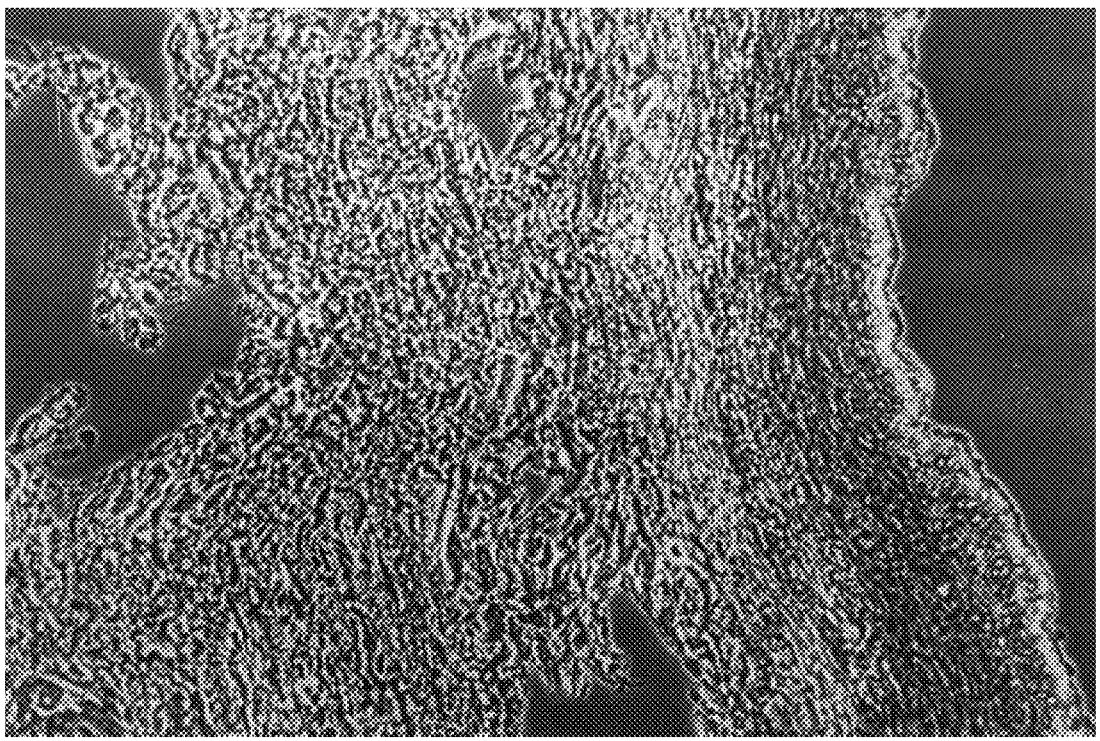
Figure 18B:
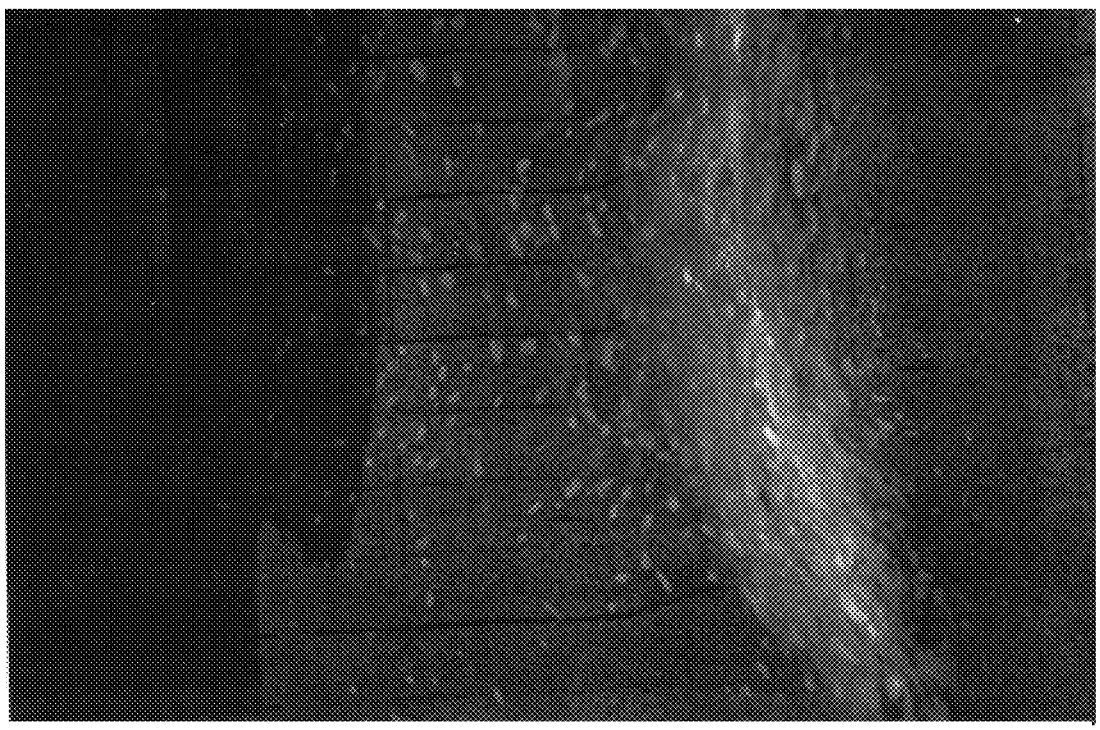
Figure 18C:
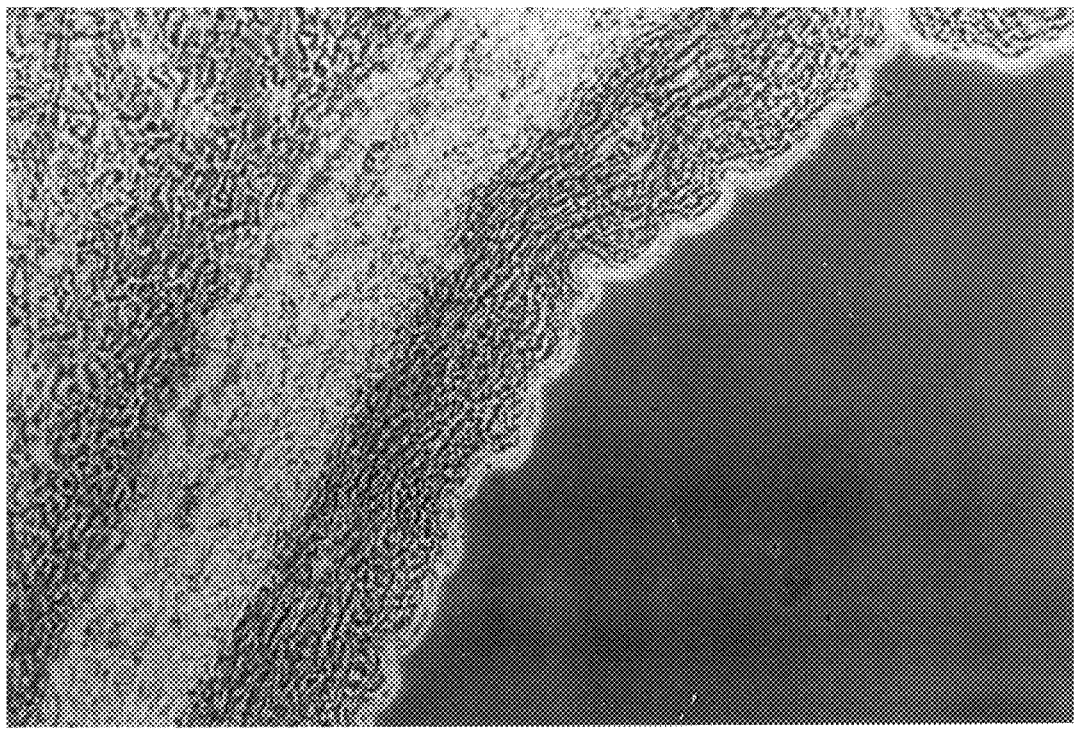
Figure 18D:
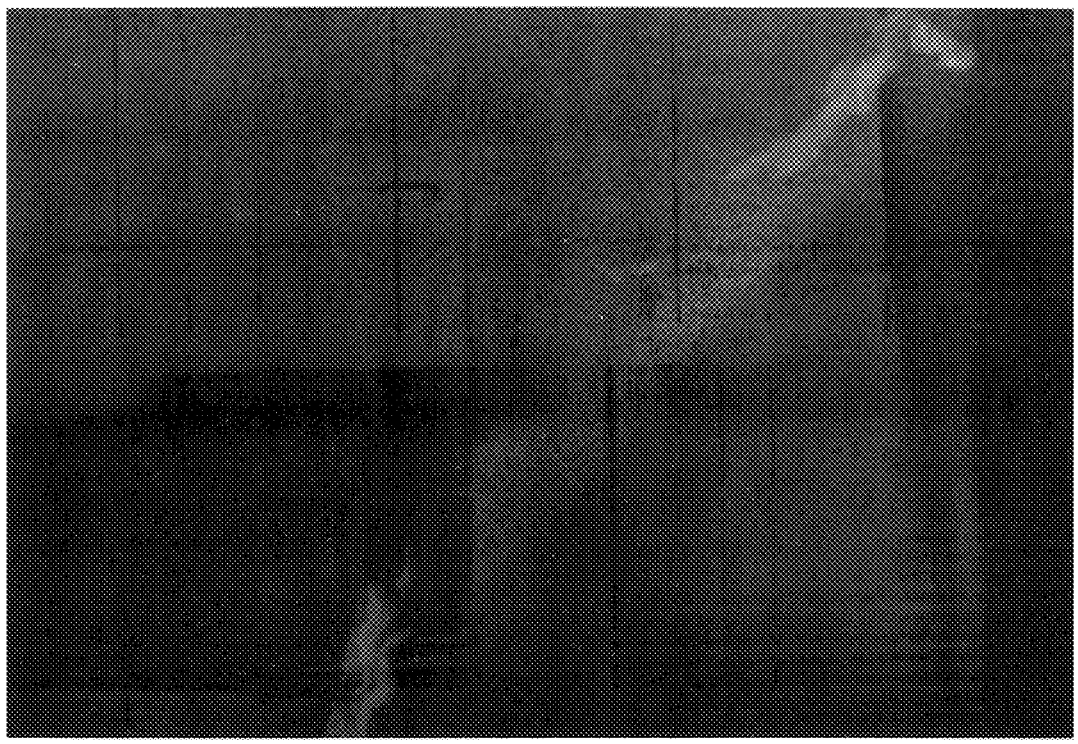
Figure 18E:
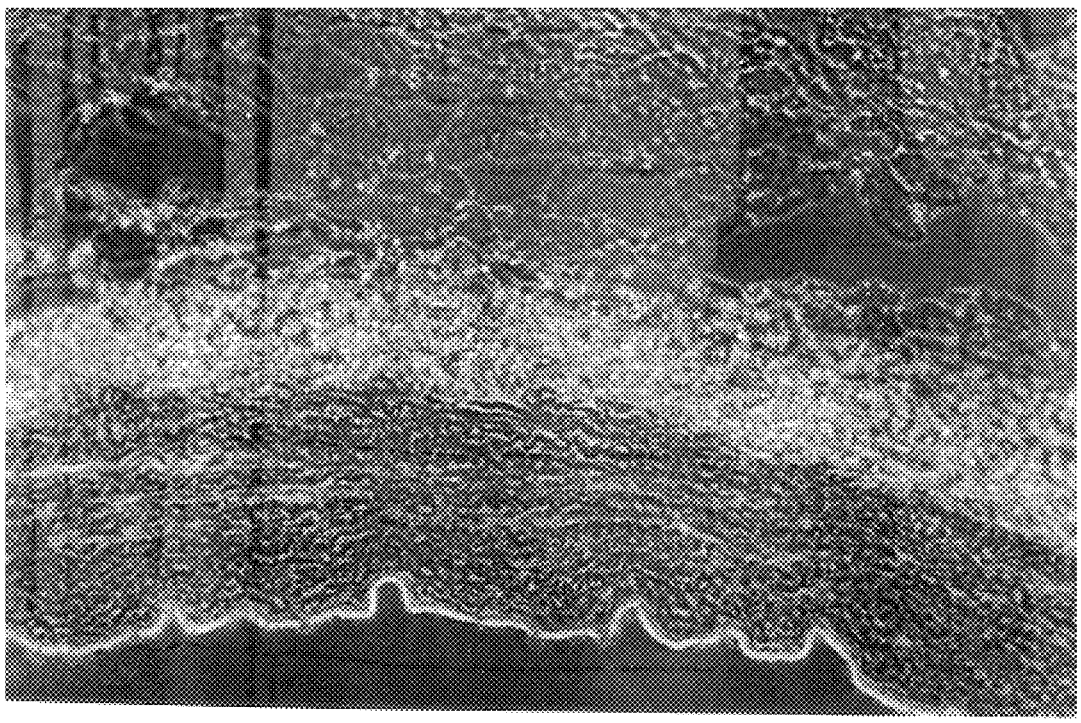
Figure 18F:
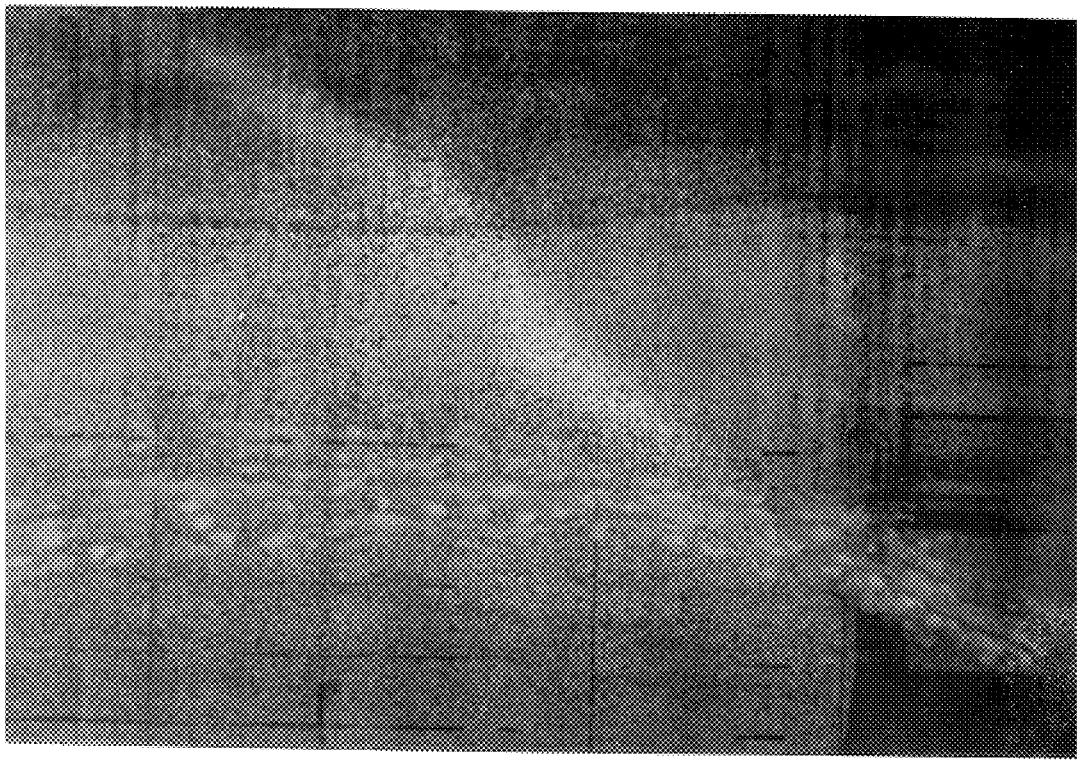

To determine oligonucleotide distribution in the arterial wall, their localization in the coronary arteries was examined at 30 minutes and 3 days after intramural administration (n=4). Fluorescein-labeled oligonucleotides were detected only in the region of injection but not in distal segments or in non-injected coronary arteries. At 30 minutes, three distinct focal patterns of oligonucleotides distribution were noted within injected segments which had previously undergone balloon denudation. Dense transmural localization involving the entire thickness of media was associated with more sparse adventitial and perivascular distribution (FIGS. 18A and 18B). In each section, oligonucleotides occupied only the portion of the arterial circumference. Subintimal nontransmural pattern was common; it was either interspersed between transmural localization or at the edges of injected segments (FIGS. 18C and 18D). Midwall nontransmural pattern was the least common and it was found adjacent to transmural localization (FIGS. 18E and 18F). The vessel adventitia was devoid of antisense oligonucleotides in sections exhibiting nontransmural distribution.

Figure 19B:
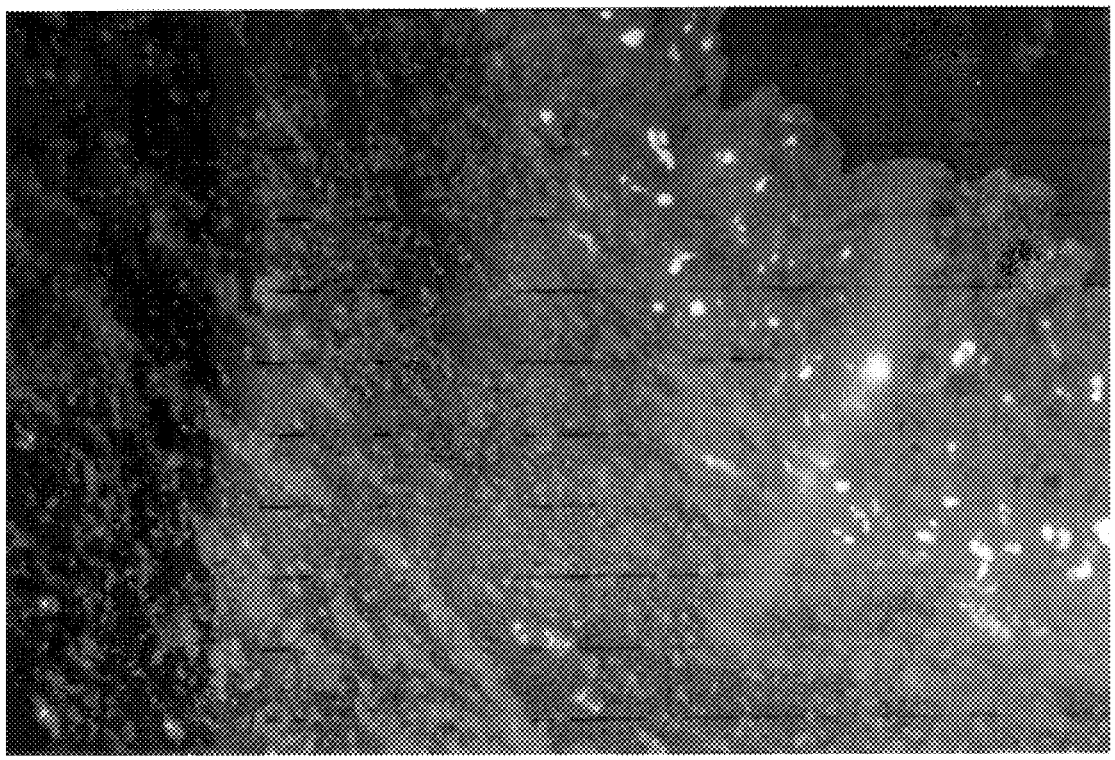

The role of preceding vascular damage in c-myc antisense oligonucleotide distribution in the arterial wall was also examined. The analysis of consecutive slides revealed that transmural distribution was the most common in the areas of dissection with oligonucleotide localization extending to immediately adjacent sections. The subintimal nontransmural pattern was usually associated with preserved vascular integrity. At 3 days, oligonucleotides were clearly visible in transmural localization (FIGS. 19A and 19B). The subintimal nontransmural distribution was less evident likely as a result of oligonucleotides washout. No evidence for linear "jet-like" localization was present either at 30 minutes or 3 days.

These data collectively point to a focal pattern of intramural distribution of oligonucleotides after pressure-driven transcatheter administration. Coronary artery dissection due to prior balloon denudation appeared to facilitate the entry and transmural distribution of oligonucleotides. The nontransmural pattern was often associated with the intact internal elastic lamina.

D. Intramural Trafficking Of Oligonucleotides In Coronary Arteries

The residence time of oligonucleotides in situ was measured to determine if antisense treatment led to oligonucleotide retention. Accordingly, to quantitatively address this issue, $^{35}$S-labeled c-myc antisense oligonucleotides were delivered using a transcatheter in porcine coronary arteries. As shown in FIG. 20, at 30 min following site-specific administration, tissue radioactivity was measured which reflects an oligonucleotide content of 2510±1436 cpm (n=6) in the vessel wall and 2163±966 cpm (n=6) in the perivascular tissue as opposed to tissue background of 17±4 cpm. Three days later, oligonucleotide-associated radioactivity increased to 3595±1672 cpm (n=4) in the vessel wall, whereas in the periadventitial tissue levels decreased to 432±201 cpm (n-4). The above sustained level of oligonucleotides was achieved despite a rapid plasma clearance ($t_{1/2}$15±2 min). The amount of detected oligonucleotides both at 30 min and 3 days corresponded to about 0.1% of total administered dose. These results indicate that pressure-driven transcatheter delivery leads to antisense oligonucleotides deposition in medial, and adventitial tissues, as well as, perivascular tissues.

E. Vascular Integrity After Intramural Administration of oligonucleotides

Figure 21A:
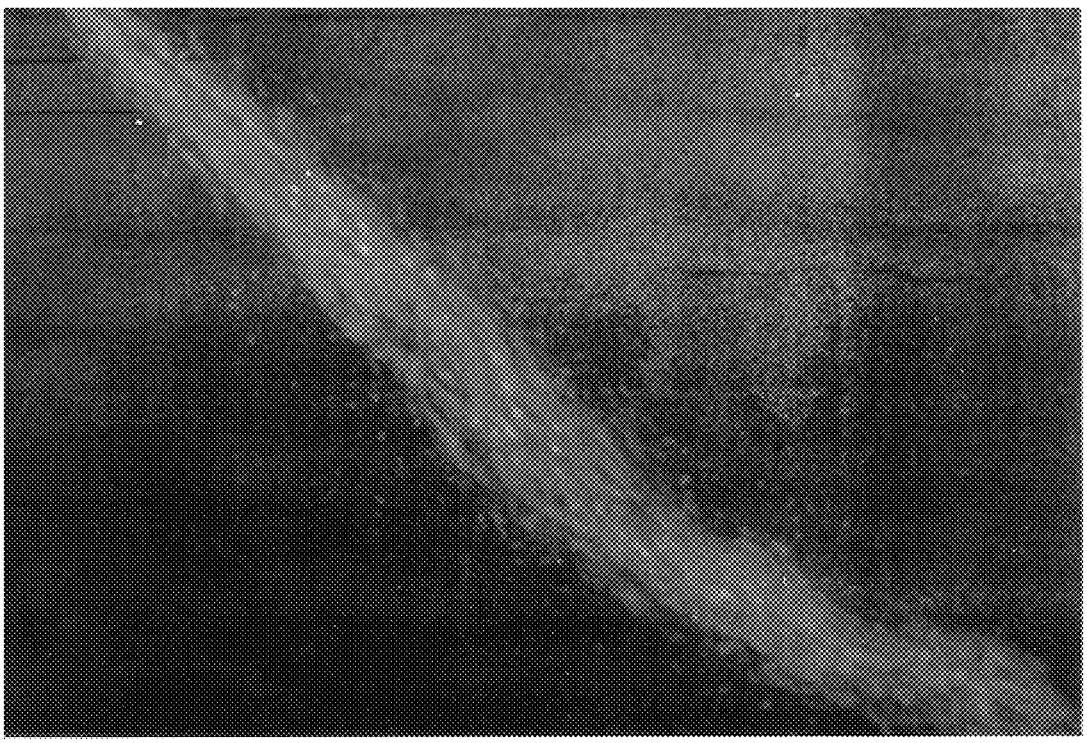
Figure 21B:
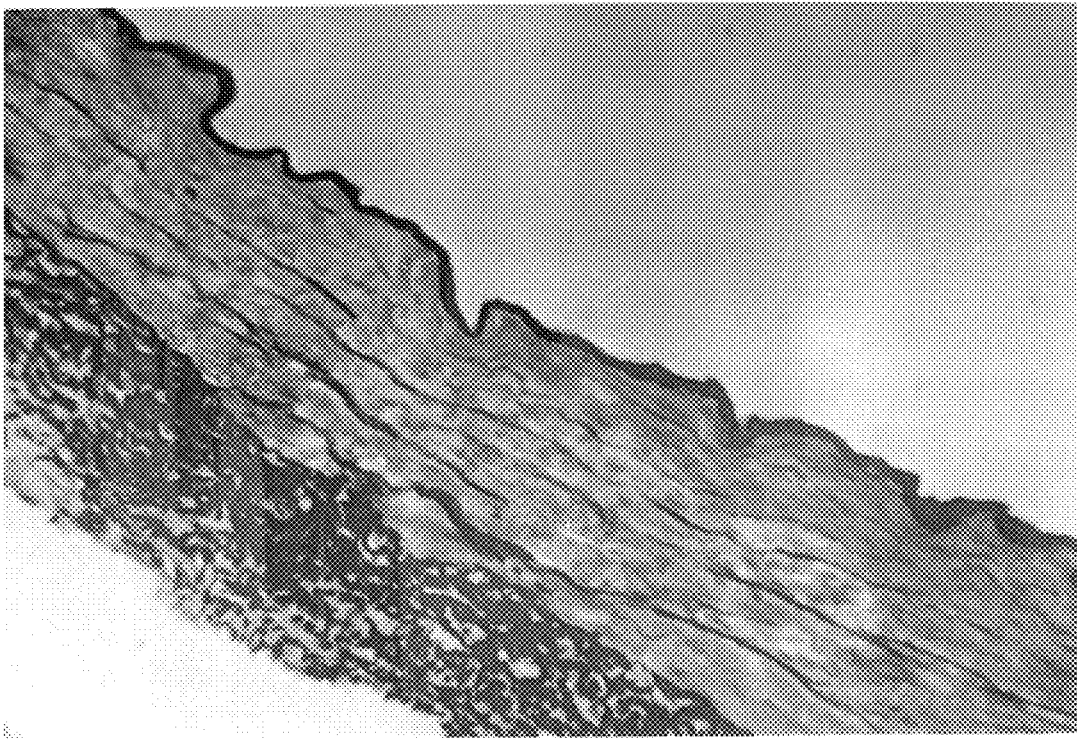
Figure 21C:
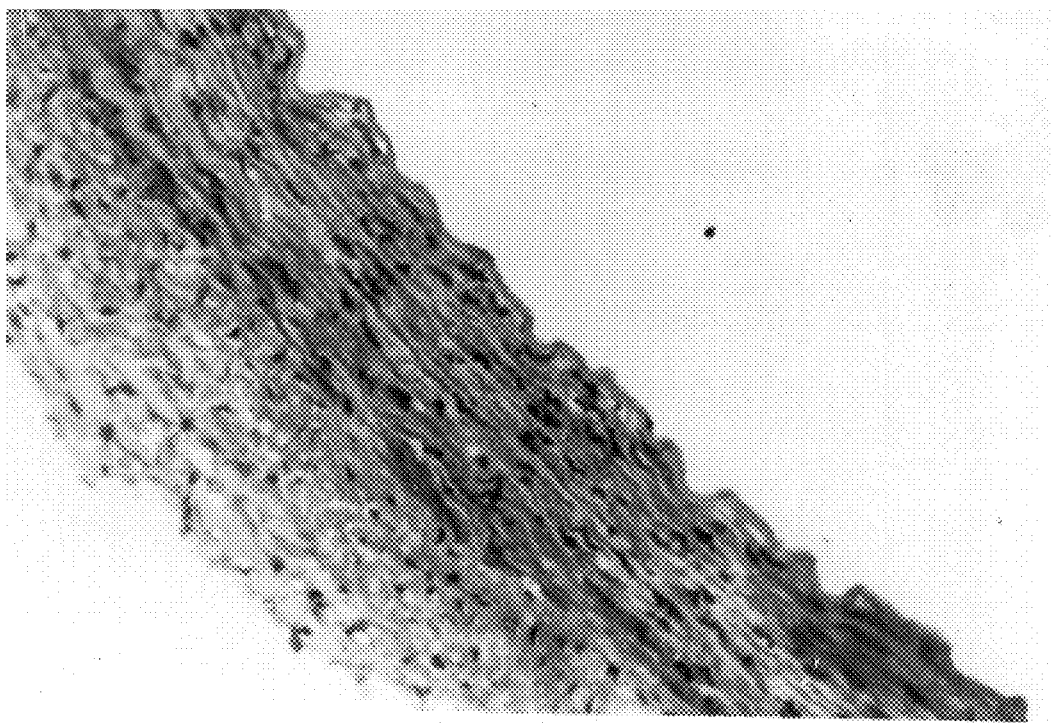
Figure 21D:
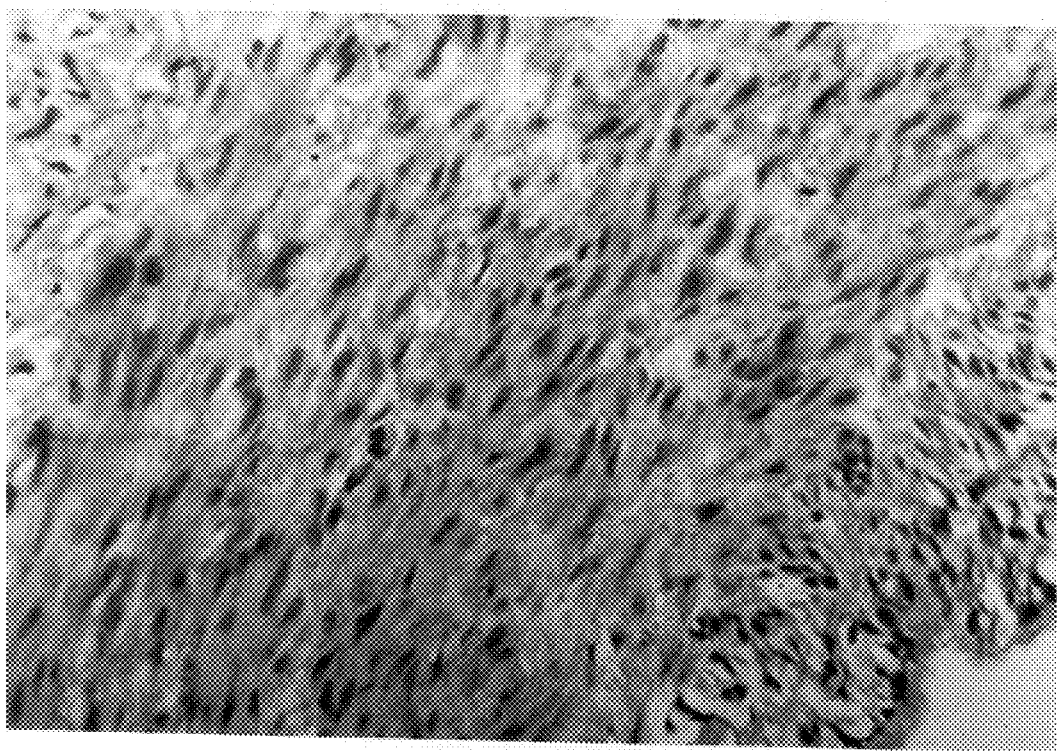

Since pressure-driven transcatheter injection of any therapeutic agent to the arterial wall may induce vascular damage the extent of damage was measured. First, using qualitative coronary angiography, non-flow limiting coronary dissection was observed in 1 out of 14 intramural injections in porcine coronary arteries notwithstanding prior injury with the oversized balloon. Second, we have utilized quantitative coronary angiography to assess luminal diameter following intramural oligonucleotides delivery (n=14). There was no significant change in luminal diameter after transcatheter oligonucleotides administration (Table V). Third, we have assessed the effects of transcatheter oligonucleotides injection using light microscopy. To this end, sections of coronary arteries with transmural distribution of oligonucleotides and no visible dissection were evaluated in order to determine subtle changes in cellular and extracellular matrix components of the vessel wall. As shown in FIG. 21, transmural distribution of oligonucleotides (FIG. 21A) was associated with the intact internal elastic lamina and elastic tissues throughout the vessel wall (FIG. 21B). A mild decrease in cytoplasmic staining and nuclear pyknosis was occasionally noted at the site of oligonucleotides retention at 30 min (FIG. 21C). These changes were not found at 3 days after the delivery (FIG. 21D).

Example XIV

Rapid Nuclear Localization of c-myc Antisense Oligonucleotides In in vitro and In Vivo human Smooth Muscle Cells This example further demonstrates the effectiveness of c-myc antisense oligonucleotide treatment in vivo by showing the rapid localization of c-myc antisense oligonucleotides in the nuclei of human smooth muscle cells both in vitro and in vivo. This time course allows for inhibition of c-myc gene activation, previously established on the order of hours (3 to 4 hours).

A. Intracellular Localization Of Carboxyfluoroscein labelled c-myc Antisense Oligonucleotides To analyze intracellular localization of fluorescent labeled oligonucleotides in vitro, laser scanning confocal microscope (model Zeiss Axiovert 100) adapted with MRC-600 krypton-argon laser (Bio-Rad) was used. The krypton-argon laser emits laser lines at excitation wavelength 488 nm. The induced fluorescent light is scanned through a 63× objective and converted to a video signal for display on a computer screen. The images were photographed off the computer screen on Kodak Ektachrome 100 films. For in vitro studies, in order to determine the time course of oligonucleotides uptake by vascular smooth muscle cells, cells were grown on chamber slides in medium containing 10% fetal bovine serum for 2 days and fluorescein-labeled oligonucleotides were added (8 $\mu$M) for 2, 30 minutes and 2 hours. Then, cells were washed 3 times with PBS and fixed in 50% acetone and 50% methanol.

B. Cellular Uptake of Antisense oligonucleotides

The intramural delivery of antisense oligonucleotides should be followed by a rapid cellular uptake of oligonucleotides in order to permit the inhibition of expression of targeted gene, in this case c-myc. As illustrated on FIG. 22, vascular smooth muscle cells demonstrate in vitro preferential nuclear localization of fluorescence 30 min following the onset of incubation with fluorescein-labeled oligonucleotides. Likewise, at 30 min following in vivo transcatheter administration, nuclear localization of oligonucleotides was noted within the media (FIG. 23) and the adventitia (FIG. 24) which demonstrates comparably rapid uptake of antisense oligonucleotides in vivo. Accordingly, intracellular uptake of antisense oligonucleotides by vascular smooth muscle cells in vitro and in vivo occurs during a critical time window available for the modulation of c-myc proto-oncogene, an important inducible gene regulating smooth muscle cells proliferation following vessel wall injury.

We claim:

1. A method of inhibiting or reducing scar formation in a tissue of an internal organ of a mammal, other than vascular tissue, the method comprising locally administering to said tissue one or more antisense oligonucleotides specific for c-myc in an amount effective to inhibit or decrease extracellular matrix protein formation.

2. The method of claim 1 wherein said extracellular matrix protein comprises collagen.

3. A method of inhibiting or reducing scar formation in the skin of a mammal comprising locally administering to tissue of said skin one or more antisense oligonucleotides specific for c-myc in an amount effective to inhibit or decrease extracellular matrix protein formation in said tissue.

4. The method of claim 3 wherein said antisense oligonucleotide is administered topically.

5. A method of inhibiting the synthesis of extracellular matrix proteins in a tissue of an internal organ of a mammal, other than vascular tissue, the method comprising locally administering to said tissue one or more antisense oligonucleotides specific for c-myc in an amount effective to inhibit or decrease extracellular matrix protein formation.

6. The method of claim 5 wherein said extracellular matrix protein comprises collagen.

7. The method of claim 5 wherein said extracellular matrix protein comprises procollagen I or pro collagen III.

8. The method of claim 5 wherein said antisense oligonucleotide is complementary to the translation initiation region of c-myc mRNA.

9. The method of claim 5 wherein said antisense oligonucleotide has a length within the range of from 12 to 40 nucleotides.

10. The method of claim 9 wherein said antisense oligonucleotide has a length within the range of from 15 to 30 nucleotides.

11. The method of claim 5 wherein said antisense oligonucleotide comprises at least one modified nucleotide.

12. The method of claim 11 wherein the antisense oligonucleotide is a phosphorothioate antisense oligonucleotide.

13. The method of claim 9 wherein said antisense oligonucleotide has a sequence selected from the group of sequences consisting of SEQ ID NO:1, SEQ ID NO:6 and SEQ ID NO:7.

14. The method of claim 13 wherein said antisense oligonucleotide has the sequence SEQ ID NO:1.

15. The method of claim 13 wherein the antisense oligonucleotide is a phosphorothioate antisense oligonucleotide.

16. A method of inhibiting the synthesis of extracellular matrix proteins in a tissue comprising skin fibroblasts comprising locally administering to said tissue one or more antisense oligonucleotides specific for c-myc in an amount effective to inhibit or decrease extracellular matrix protein formation.

17. The method of claim 16 wherein said antisense oligonucleotide is administered topically.

18. The method of claim 5 wherein said tissue is connective tissue.

19. The method of claim 18 wherein said local administration comprises delivery to connective tissue using a rigid, noncollapsable channel.

20. The method of claim 18 wherein said local administration comprises delivery to human connective tissue using iontophoresis to release said antisense oligonucleotide.

21. The method of claim 5 wherein said local administration comprises delivery with a catheter or a coated stent.

22. The method of claim 5 wherein said local administration comprises using a biodegradable polymer, non-biodegradable polymer or stent to release said antisense oligonucleotide.

23. The method of claim 5 further comprising administering a therapeutically effective amount of one or more antisense oligonucleotides specific for c-myb.

24. The method of claim 1 wherein the tissue comprises gastrointestinal organ tissue, or comprises biliary duct, lung, liver, ureter, urethra or bladder tissue.

25. The method of claim 5 wherein the tissue comprises gastrointestinal organ tissue, or comprises biliary duct, lung, liver, ureter, urethra or bladder tissue.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 15 nucleotides
       (B) TYPE: nucleic acid
       (C) STRANDEDNESS: single
       (D) TOPOLOGY: linear (xi) SEQUENCE DESCRIPTION: SEQ ID NO: 1:

AACGTTGAGG GGCAT                                               15

(2) INFORMATION FOR SEQ ID NO: 2:

(i) SEQUENCE CHARACTERISTICS:
       (A) LENGTH: 15 nucleotides
       (B) TYPE: nucleic acid
       (C) STRANDEDNESS: single
       (D) TOPOLOGY: linear (xi) SEQUENCE DESCRIPTION: SEQ ID NO: 2:

ATGCCCCTCA ACGTT                                               15

(2) INFORMATION FOR SEQ ID NO: 3:

(i) SEQUENCE CHARACTERISTICS:
       (A) LENGTH: 15 nucleotides
       (B) TYPE: nucleic acid
       (C) STRANDEDNESS: single
       (D) TOPOLOGY: linear (xi) SEQUENCE DESCRIPTION: SEQ ID NO: 3:

AACGTGGATT GGCAG                                             15

(2) INFORMATION FOR SEQ ID NO: 4:

(i) SEQUENCE CHARACTERISTICS:
       (A) LENGTH: 15 nucleotides
       (B) TYPE: nucleic acid
       (C) STRANDEDNESS: single
       (D) TOPOLOGY: linear (xi) SEQUENCE DESCRIPTION: SEQ ID NO: 4:

GAACGGAGAC GGTTT                                             15

(2) INFORMATION FOR SEQ ID NO: 5:

(i) SEQUENCE CHARACTERISTICS:
       (A) LENGTH: 24 nucleotides
       (B) TYPE: nucleic acid
       (C) STRANDEDNESS: single
       (D) TOPOLOGY: linear (xi) SEQUENCE DESCRIPTION: SEQ ID NO: 5:

TATGCTGTGC CGGGGTCTTC GGGC                                 24

(2) INFORMATION FOR SEQ ID NO: 6:

(i) SEQUENCE CHARACTERISTICS:
       (A) LENGTH: 20 nucleotides
       (B) TYPE: nucleic acid
       (C) STRANDEDNESS: single -continued (D) TOPOLOGY:  linear (xi) SEQUENCE DESCRIPTION:  SEQ ID NO: 6:

GGGAGAGTCG CGTCCTTGCT                                                    20

(2) INFORMATION FOR SEQ ID NO: 7:

(i) SEQUENCE CHARACTERISTICS:
            (A) LENGTH:  20 nucleotides
            (B) TYPE:  nucleic acid
            (C) STRANDEDNESS:  single
            (D) TOPOLOGY:  linear (xi) SEQUENCE DESCRIPTION:  SEQ ID NO: 7:

TCATGGAGCA CCAGGGGCTC                                                    20